US012365102B2

(12) United States Patent
    Collet

(10) Patent No.: US 12,365,102 B2
(45) Date of Patent: *Jul. 22, 2025

(54) HIGH ACCURACY MOLDED NAVIGATION ARRAYS, SYSTEMS, AND METHODS

(71) Applicant: DePuy Ireland Unlimited Company, Ringaskiddy (IE)

(72) Inventor: Hervé Collet, Chatenay (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/640,478

(22) Filed: Apr. 19, 2024

(65) Prior Publication Data

US 2024/0261986 A1    Aug. 8, 2024

Related U.S. Application Data

(63) Continuation of application No. 17/542,936, filed on Dec. 6, 2021, now Pat. No. 11,992,941.

(Continued)

(51) Int. Cl.
    *B25J 19/04*      (2006.01)
    *B25J 5/00*       (2006.01)
    (Continued)

(52) U.S. Cl.
    CPC ............ *B25J 19/023* (2013.01); *B25J 5/007* (2013.01); *B25J 11/008* (2013.01); *B25J 19/04* (2013.01)

(58) Field of Classification Search
    CPC ........ B25J 19/04; B25J 19/023; B25J 11/008; A61B 90/39; A61B 2034/2059;
    (Continued)

(56) References Cited

U.S. PATENT DOCUMENTS 8,073,528 B2    12/2011    Zhao et al.
9,560,250 B2     1/2017    Furihata et al.
(Continued)

FOREIGN PATENT DOCUMENTS

EP    1640750 A1    3/2006
WO    2013115640 A1    8/2013

OTHER PUBLICATIONS

Liao et al., Surgical navigation by autostereoscopic image overlay of integral videography, 2004, IEEE, p. 114-121 (Year: 2004).*

(Continued)

*Primary Examiner* — Marc McDieunel
(74) *Attorney, Agent, or Firm* — Condo Roccia Koptiw LLP

(57) ABSTRACT

Systems, methods, and devices are described for high accuracy molded navigation arrays. In a first embodiment, a navigation array is formed by molding, as a single component, an array having a plurality of marker regions. The marker regions include a reflective layer disposed thereon. In other embodiments, a navigation array is formed by molding over a frame having a plurality of marker elements. In still other embodiments, a navigation array is formed by molding over individual marker elements. In certain embodiments, a navigation array is formed by molding a frame with a plurality of voids and subsequently molding marker elements into each void where the marker elements include a reflective layer disposed thereon. In some embodiments, a navigation array is formed by molding a plurality of marker elements on a frame and disposing a reflective layer on the marker elements.

20 Claims, 19 Drawing Sheets

Related U.S. Application Data

(60) Provisional application No. 63/124,687, filed on Dec. 11, 2020.

(51) Int. Cl.
   *B25J 11/00* (2006.01)
   *B25J 19/02* (2006.01)

(58) Field of Classification Search
   CPC ............ A61B 2090/3983; A61B 34/30; A61B 2017/00526; A61B 2034/2068; A61B 2034/2055
   See application file for complete search history.

(56) References Cited

U.S. PATENT DOCUMENTS

| | | | |
|---|---|---|---|
| 10,873,739 B2 | 12/2020 | Kumagai et al. | |
| 11,253,322 B2 | 2/2022 | Van Beek et al. | |
| 11,311,342 B2 | 4/2022 | Parihar et al. | |
| 11,424,027 B2 | 8/2022 | Shelton, IV | |
| 11,564,756 B2 | 1/2023 | Shelton, IV et al. | |
| 11,576,677 B2 | 2/2023 | Shelton, IV et al. | |
| 11,918,313 B2 * | 3/2024 | Johnson | A61B 34/30 |
| 11,992,941 B2 * | 5/2024 | Collet | B25J 19/023 |
| 12,076,091 B2 * | 9/2024 | Calloway | A61B 34/25 |
| 2009/0099445 A1 | 4/2009 | Burger | |
| 2018/0250820 A1 | 9/2018 | Shimodaira et al. | |
| 2019/0357986 A1 | 11/2019 | Morgan et al. | |
| 2020/0237265 A1 | 7/2020 | Jaisson | |
| 2022/0125520 A1 * | 4/2022 | Crawford | A61B 46/10 |
| 2022/0292702 A1 | 9/2022 | Yoshikuwa et al. | |
| 2024/0197407 A1 * | 6/2024 | Decker | A61F 2/46 |

OTHER PUBLICATIONS

Chapuis et al., A New System for Computer-Aided Preoperative Planning and Intraoperative Navigation During Corrective Jaw Surgery, 2007, IEEE, p. 274-287 (Year: 2007).*

Wang et al., Augmented Reality Navigation With Automatic Marker-Free Image Registration Using 3-D Image Overlay for Dental Surgery, 2014, IEEE, p. 1295-1304 (Year: 2014).*

Pallath et al., Real time computer assisted surgical navigation, 2012, IEEE, p. 128-133 (Year: 2012).*

Goral, Adrian, "Assessment of a Markerless Optical Tracking Technique for Computer-Assisted Hip Surgery", IEEE, 2018, 6 pages.

Hussain, et al., "Contribution of Augmented Reality to Minimally Invasive Computer-Assisted Cranial Base Surgery", IEEE Journal of Biomedical and Health Informatics, vol. 24, No. 7, Jul. 2020, pp. 2093-2106.

Lorsakui, et al., "Toward Robot-Assisted Dental Surgery: Path Generation and Navigation System Using Optical Tracking Approach", Proceedings of the 2008 IEEE, International Conference on Robotics and Biomimetics, Bangkok, Thailand, Feb. 21-26, 2009, pp. 1212-1217.

Ren, et al., "Marker-Based Surgical Instrument Tracking Using Dual Kinect Sensors", IEEE Transactions on Automation Science and Engineering, vol. 11, No. 3, Jul. 2014, pp. 921-924.

* cited by examiner

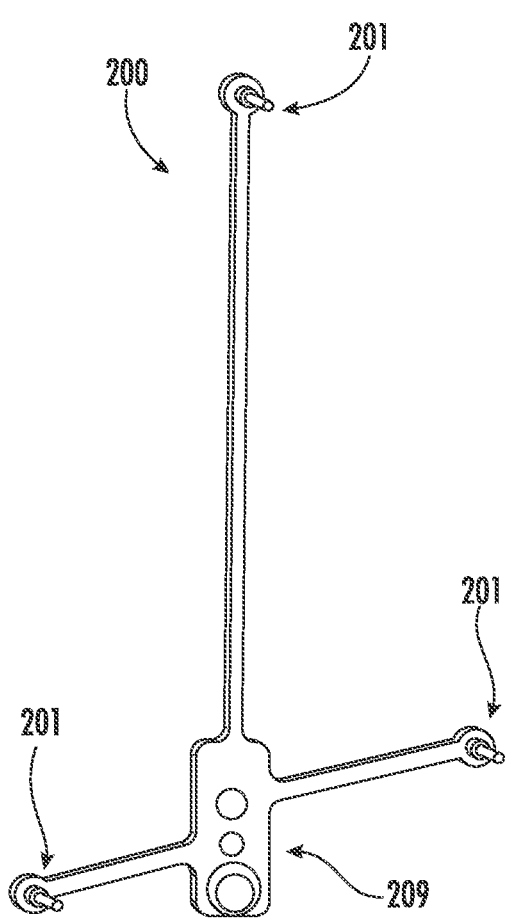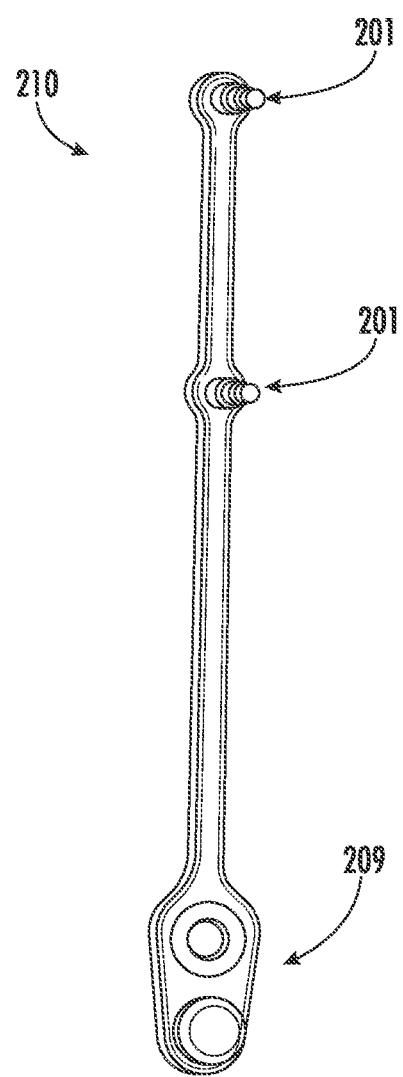
FIG. 2A
FIG. 2B

HIGH ACCURACY MOLDED NAVIGATION ARRAYS, SYSTEMS, AND METHODS

CROSS REFERENCE TO RELATED APPLICATION

This application is a continuation of U.S. patent application Ser. No. 17/542,936 (now U.S. Pat. No. 11,992,941), which claims priority to U.S. Provisional Patent Application No. 63/124,687, filed Dec. 11, 2020, the disclosures of each of which are incorporated by reference herein in their entireties.

BACKGROUND

Many different surgical procedures utilize some form of surgical navigation or tracking to aid in positioning surgical instruments relative to portions of patient anatomy during a procedure. Robotic or robot-assisted surgical procedures are an important example of such a surgical procedure, as surgical navigation is crucial for correctly positioning a robotically controlled or assisted surgical instrument relative to a patient. For example, in such a system, optical navigation or tracking systems may utilize stereoscopic sensors to detect infra-red (IR) light reflected or emitted from one or more optical markers affixed to surgical instruments and/or portions of a patient's anatomy. A navigation array or tracker having a unique constellation or geometric arrangement of reflective elements may be coupled to a surgical instrument and, once detected by stereoscopic sensors, the relative arrangement of the elements in the sensors' field of view, in combination with the known geometric arrangement of the elements, may allow the system to determine a three-dimensional position and orientation of the tracker and, as a result, the instrument or anatomy to which the tracker is coupled. For example, the array may be mounted (e.g., integrally or removably) on an instrument, and the instrument may be received and/or controlled by a robot arm. Navigation systems may identify a position of the instrument.

Navigation arrays often comprise multi-component structures that include at least a frame and reflective navigation markers adapted to be coupled thereto before use. In some cases, for example, a navigation array may include posts or protrusions mounted on the frame, the posts configured to be received within a recess formed in a reflective navigation marker, and the frame and marker components joined together. However, as accuracy is a paramount consideration in surgical navigation, it can be appreciated that multi-component structures may be associated with certain drawbacks. For example, poor dimensional tolerances of either the frame, reflective navigation marker, or user error in assembly, can each affect accuracy, and thus impact navigation performance of a robotic surgical system. Moreover, some navigation arrays experience significant forces (e.g., such as vibration) during the surgical procedure, which may allow multi-component structures to become relatively loosened, which affects accuracy.

Accordingly, there is a need for improved systems, methods, and devices for creating high accuracy navigation arrays that may be utilized to track (e.g., accurately) surgical instruments, patient anatomy, or other components during a surgical procedure.

SUMMARY

Systems, methods, and devices are disclosed for a navigation array, such as for use in a computer-assisted surgical system, the array comprising a monolithic array body comprising a nonreflective frame region, and a plurality of spaced apart marker regions, wherein each of the marker regions has an associated reflective element configured to be detected and tracked by an optical tracking sensor.

In yet another example, a computer assisted surgical system comprises the above-described navigation array, an optical tracking unit associated with at least one optical tracking sensor, and a control unit, wherein the control unit may be adapted to utilize a predetermined fixed geometric relationship between the marker regions and detected positions of the marker regions to determine a three-dimensional position and orientation of the navigation array. The computer assisted surgical system may further comprise a robot arm and a surgical instrument mounted to the robot arm. The navigation array may be adapted to be mounted to the robot arm or the surgical instrument.

In yet another example, a method manufacturing a navigation array comprises injection molding, in a single operation, the monolithic array body. In yet another example, a method manufacturing a navigation array comprises over molding the monolithic array body over a navigation marker sub-assembly.

BRIEF DESCRIPTION OF THE DRAWINGS

FIGS. 2A and 2B show a pair of surgical navigation array frames that may be part of multi-component (e.g., non-monolithic) navigation array;

DETAILED DESCRIPTION

Figure 1:
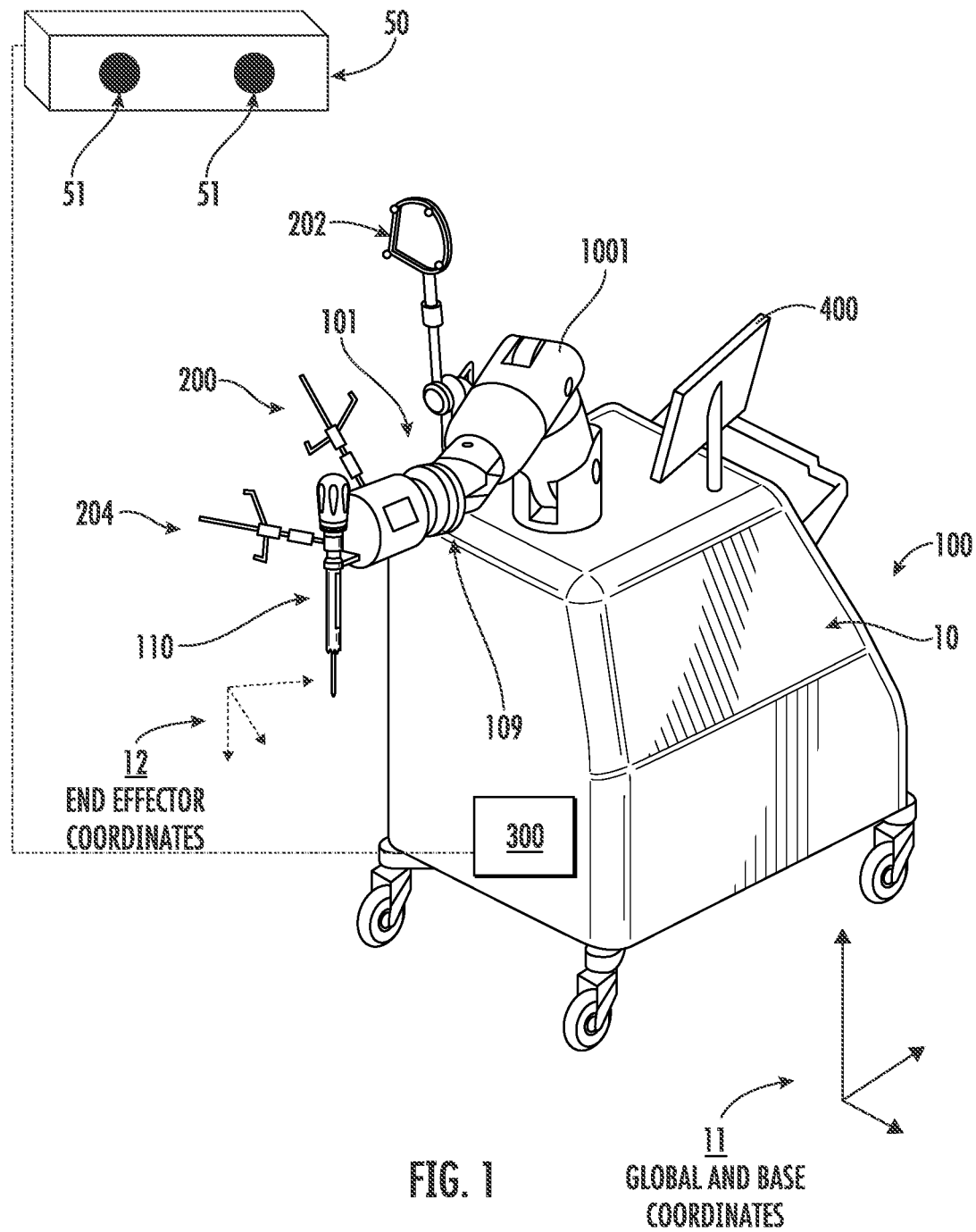
FIG. 1 shows a schematic of a robotic surgical system.

Devices, systems, and methods for high accuracy navigation arrays are disclosed herein. In some embodiments, high accuracy navigation arrays are created by molding the array as a monolithic unit that includes a plurality of navigation marker regions spaced apart in a desired geometric relationship. "Monolithic," as used herein, refers to cast or molded as a single piece (e.g., a single part), preferably, injection-molded. As will be described, the monolithic navigation arrays of the present disclosure may be molded from a single material or may be of multiple materials molded together.

Molding a navigation array may provide advantages because the single part's dimensions may be tightly controlled with regard to tolerances and the molding process may be highly repeatable. In addition, there is greater flexibility to manufacture navigation arrays of various sizes according to need (e.g., for affixing to different size instrumentation, anatomy, or other components). The devices, systems, and methods disclosed herein provide a variety of different molded high accuracy navigation arrays, including arrays molded using a single material, arrays molded with multiple materials for different regions, arrays molded over other parts, such as an assembly of pre-existing navigation markers, various array tips or other inserts, etc., and arrays molded over a plurality of individual or separate components, such as an array molded over a plurality of pre-existing navigation markers that are not coupled to one another in an assembly.

Example embodiments of the present disclosure provide methods of manufacturing navigation arrays with a consistently low tolerances by manufacturing the array and the navigation markers into one single part using an injection molding process, where the tolerance of the molding operation is primary responsible for the resultant tolerance in the position between the navigation markers. The molded array may have multiple portions, or navigation marker regions, that are designed to be clear (e.g., formed from polycarbonate) and subsequently receive a reflective treatment in order to form a navigation marker in the clear region of the array. For example, in molding a navigation array, multiple regions may be formed as full or half sphere lenses, with exteriors of those regions receiving a reflective material coating in a subsequent step to form a navigation marker (e.g., a lens and a reflective surface behind the lens). The use of a single molding operation to define the relative locations of the navigation markers may enable the accuracy between the reflective portions to achieve desired tolerances, e.g., +/−0.05 mm in some embodiments. Moreover, because injection molding processes are repeatable using the same mold, the consistency of the tolerances across multiple arrays formed by this process may be extremely high.

Each of these arrays may be a monolithic component that lacks a mechanical interface capable of easy disassembly or re-assembly. As noted above, molding the navigation arrays disclosed herein as a single piece may provide distinct advantages in eliminating drawbacks of conventionally-assembled arrays with regard to positional tolerancing, etc. This may be important for optimal navigation tracking performance, as surgical navigation systems may require tolerances below about 0.1 mm for placement of reflective elements in some embodiments, and below about 0.05 mm for placement of reflective elements in certain embodiments. Conventional approaches, e.g., multi-component navigation arrays, may often fail to achieve better than about 0.15 mm tolerance in positioning reflective elements, and in some embodiments may be produce positioning tolerance of about 0.2 mm or greater in positioning reflective elements. This may introduce errors and inaccuracies in tracking instruments, anatomy, or other components coupled to such navigation arrays.

The presently disclosed navigation arrays may be employed with computer-assisted surgical (CAS) systems, for example, robotic surgical systems. Such systems may utilize any of surgical navigation/tracking and robot control or assistance to monitor or control movement of one or more surgical instruments during a procedure. While the illustrated embodiments and accompanying description do not make particular reference to a specific surgery, the systems and methods described herein may be utilized in various applications involving robotic, robot-assisted, and non-robotic operations where computer-assisted tool location are required and precise adjustment of tool position may be appropriate. Example applications include knee surgery, e.g., total knee arthroplasty (TKA) or unicompartmental knee arthroplasty (UKA), hip surgery, e.g., hip arthroplasty, shoulder surgery, spine surgery, etc. The teachings of the present disclosure may be applied to such procedures; however, the systems and methods described herein are not limited to these applications.

FIG. 1 shows a schematic of a robotic surgical system, comprising a robotic device 100, including a surgical robot arm 1001, that includes an attached tool end effector 110 and a plurality of arm segments 101 connected by rotatable or otherwise articulating joints 109. A distal-most segment of the robot arm may include a navigation array 200 mounted thereto adjacent to the tool end effector 110. As can be appreciated, positions of the end effector can be determined with respect to the patient or to the robotic device.

A global coordinate system 11 of the robotic device 100 may be defined, as well as an end effector coordinate system 12. The global coordinate system 11 may be defined in different ways and, in some embodiments, may use the location of a base 10 of the robotic device 110, which may or may not itself be stationary, as an origin. The location of the distal-most arm segment of the robotic device may be calculated by receiving a position signal from an encoder in each joint 109 and/or by measuring a position of the navigation array 200 to directly detect the position of the arm segment and determine the position of the distal end thereof in the global coordinate system. In some instances, a measured coordinate system of the navigation array 200 may be different from the global coordinate system 11 and calculations may be utilized to harmonize the two coordinate systems. In some embodiments, the measured coordinate system may be used as the global coordinate system 11.

The end effector coordinate system 12 may be defined in different ways but may refer to the position and orientation of the tool end effector 110 with respect to the operation of the tool end effector (e.g., if the tool end effector includes a cutting bit, the cutting direction may be along an "up" or "down" axis that might be defined by, e.g., a longitudinal axis of the tool). The tool end effector 110 held by the robotic device 100 may be constrained to move about the distal end of the distal-most arm segment such that the summation of the positions of joints 109 may define the location of the end effector coordinate system 12 in the global coordinate system 11 with respect to a control system of the joints 109 to control movement of the tool end effector 110.

Accordingly, the robotic device 100 may be connected to a control unit 300 that controls, inter alia, the actuation of each joint 109 in order to position the tool end effector 110. The control unit 300 typically comprises power supply, AC/DC converters, motion controllers, and other components to power the motors of the actuation units in each joint 109, as well as fuses, real-time control system interface circuits, and other components typically included in surgical robotic devices. Further, the present disclosure is also contemplated to include use of such instruments by surgical robots, by users with some degree of robotic assistance, and without involvement of surgical robots or robotic assistance (e.g., where solely surgical navigation/tracking is utilized).

Further, in some embodiments additional and/or alternative navigation arrays may be employed in addition to, or in place of, the navigation array 200 shown attached to a distal-most arm segment 101 of the robot arm 1001. For example, in some embodiments a navigation array 202 may be coupled to another component of the robotic device, such as a base of the robot arm 1001 in embodiments where the robot is mobile. Still further, a navigation array 204 may be coupled to the tool end effector itself. In embodiments where a single tool is provided, the array 204 may be coupled directly thereto.

A tracking unit 50 is provided, such that the relative pose or three-dimensional position and orientation of the navigation arrays 200, 202, and/or 204 (or other arrays) may be tracked in real time and shared to the control unit 300 and any additional planning or control system. In some instances, coordinate systems may be attached to the robotic device 100 via the navigation array 200, the end effector 110 via the array 204, and an anatomical structure (not shown). The tracking unit 50 may measure the relative motions between any and all coordinate systems in real time. Real time may, in some embodiments, mean high frequencies greater than twenty Hertz, in some embodiments in the range of one hundred to five hundred Hertz, with low latency, in some embodiments less than five milliseconds. For example, the navigation arrays may include, for example, optical trackers comprising reflective or active markers detected by a sensor 51 in view of the surgical field. The tracking unit 50 may include a passive optical tracker consisting of, for example, a constellation of reflective tracking elements having a fixed geometric relationship that may be coupled to a portion of patient anatomy, a surgical instrument, or other component to be tracked. The tracking unit 50 may include a stereoscopic sensor having two or more physically separated detectors 51 that may be used to detect light reflected off each of the tracking elements (e.g., reflected infra-red (IR) light in some embodiments). The sensor 51, in some embodiments in conjunction with other information processing components such as the control unit 300, may utilize the known fixed geometric relationship between the tracking elements and the detected positions of the tracking elements to determine a precise three-dimensional position and orientation of the navigation array(s), and therefore, of the entity coupled to the array.

In some embodiments, in place of, or in addition to, the above-described reflective optical tracking, optical tracking may be employed using active light emitters, such as light emitting diodes (LEDs). In other embodiments, electromagnetic trackers may be employed, while in still other embodiments any of inertial sensors using gyroscopic measurements, ultrasonic sensors, radio-frequency identification (RFID) sensors, or other known sensors may be employed.

FIGS. 2A and 2B show a pair of surgical navigation array frames 200 (a three-marker frame) and 210 (a two-marker frame) that may be part of multi-component (e.g., non-monolithic) navigation arrays. Such arrays have posts 201 to receive markers, such as the above-described optical trackers (not depicted). For example, in many instances navigation arrays make use of commercially available optical reflective elements, such as the NDI Radix™ Lens, which have a body with a hemispherical polycarbonate lens opposite a larger hemispherical element with a reflective surface that is visible through the hemispherical lens. Corresponding recesses of the optical trackers receive the posts 201 and the two components may be joined using adhesives, ultrasonic welding, mechanical fastening (e.g., threads), etc. However, it may be difficult to position optical markers relative to the navigation array frames in a manner that achieves tolerances needed for optimal surgical navigation tracking performance. For example, in some cases a recess formed in an optical marker may be larger than the post 201. As a result, the optical marker (e.g., reflective navigation marker) may move about the post during assembly and end up in a position sufficiently far from its desired position. Further, tolerances for each component may stack or add together to produce a more significant variation in positioning. As can be appreciated, in an array that requires a post to attach to the marker (see FIGS. 2A and 2B) typically results in one-sided navigation markers, so that separate "left" and "right" navigation arrays are necessary to point the marker toward an expected camera location.

Figure 3A:
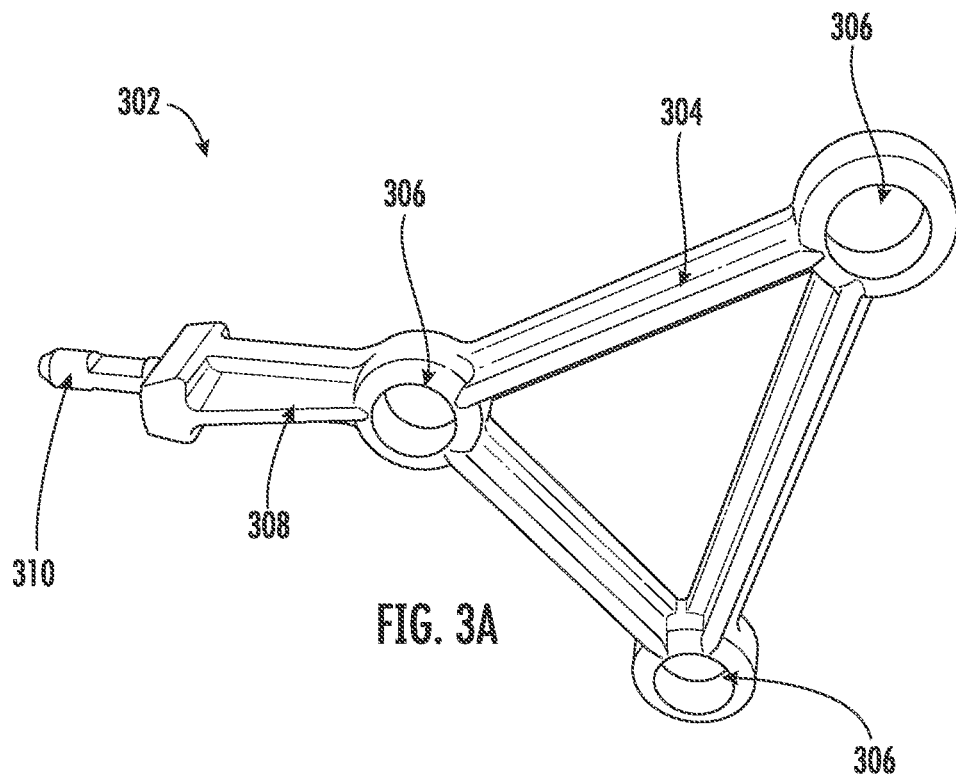
FIGS. 3A and 3B show a monolithic navigation array.
Figure 3B:
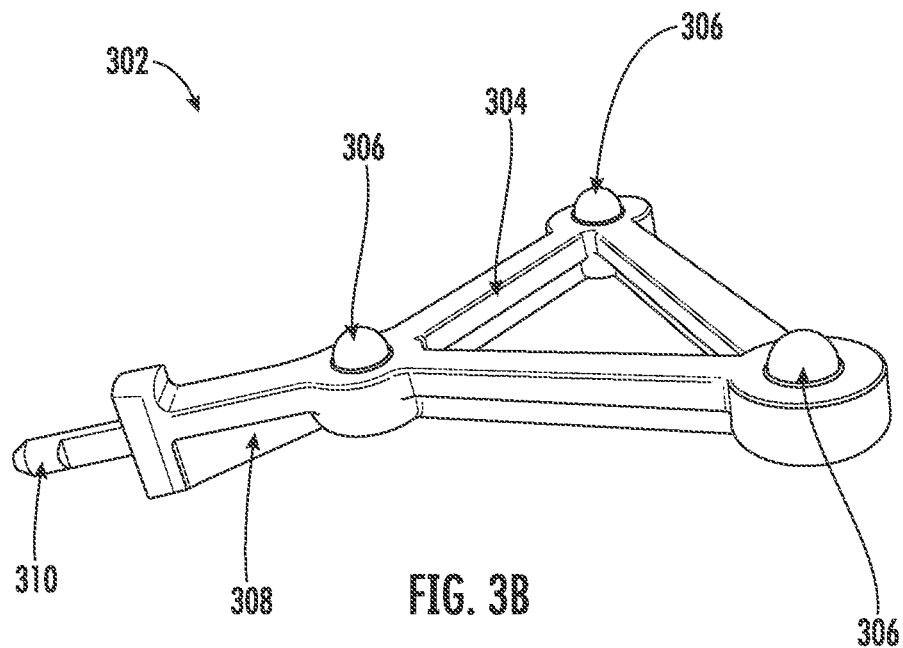

FIGS. 3A and 3B illustrate an embodiment of a monolithic navigation array 302 according to the present disclosure that may exhibit high accuracy and address the drawbacks noted above. The illustrated embodiment is a single molded component that includes a frame 304 and a plurality of marker regions 306 located a distance apart from each other. The array 302 may have any of a variety of shapes and sizes. As illustrated, the frame 304 has a generally triangular shape, casting the three marker regions 306 in a unique constellation of predetermined dimensions. Fewer or additional marker regions may be included and the shape of the frame 304 may be adjusted accordingly to accommodate the marker regions 306 and position them in a unique constellation of predetermined dimensions. Each marker region 306 may include a partial sphere that may have a hemispherical shape.

The array 302 may be molded in a single operation, e.g., by injection molding using any of a variety of suitable polymers, such as Polysulfone (PSU), Polyether Ether Ketone (PEEK), etc. to make a plastic. Further, the marker regions 306 may be provided with a reflective material (e.g., coating) after molding to afford optical reflective navigation markers, such that a tracking unit (such as the tracking unit 50 of FIG. 1) may detect them. The remainder of the frame 304 of the array 302 may have a matte finish that is not detectable. A neck 308 of the array 302 terminates in a distal end 310. The end 310 may be configured to couple with, e.g., a surgical instrument to be tracked or navigated. Alternatively, the end 310 may be pointer tip or other tip that may be used to register anatomy or other components in the surgical field with the navigation system.

Figure 4A:
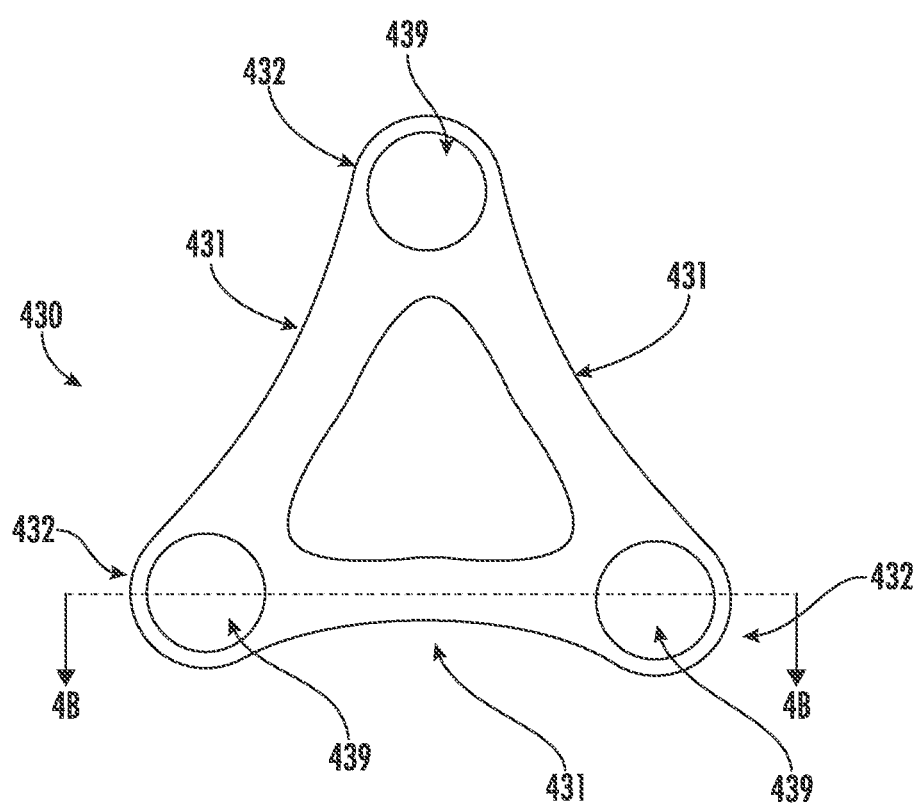
FIG. 4A shows another embodiment of a monolithic navigation array.

FIG. 4A is an illustration of another embodiment of a monolithic navigation array 430 that includes a frame 431 and a plurality of marker regions 432 located a distance apart from each other. A navigation marker lens 439 is disposed in each of the marker regions 432. The frame 431, marker regions 432, and navigation marker lens 439 may be molded from a single material in a single molding operation to control the position of each navigation marker lens 439 with respect to each other to the lowest tolerance possible (e.g., the tolerance of the molding machine and/or molding operation).

Figure 4B:
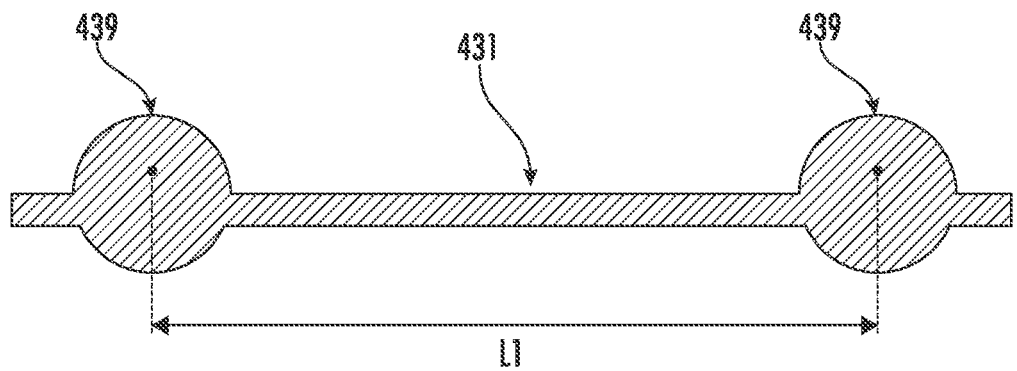
FIGS. 4B and 4C show sectional views of the monolithic navigation array of FIG. 4A after molding and after application of a reflective material in select areas, respectively.

FIG. 4B shows a cross-section of the array 430 with the distance between each navigation marker lens 439 indicated as L1. The tolerance of this distance L1, and therefore the overall accuracy of the navigation array, is limited only by the molding operation and the material properties of the material used to mold the array 430. As such, the array 430 is a highly accurate array.

Figure 4C:
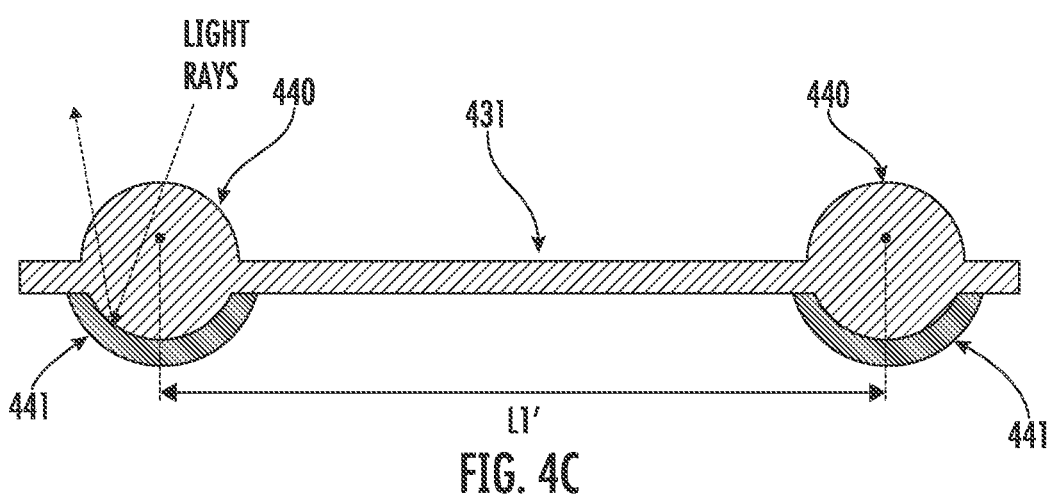

At FIG. 4C, a rear side of each navigation marker lens 439 may be coated with a reflective material 441 in order to form an optical marker 440 from the combined arrangement of the navigation marker lens 439 and reflective material 441. FIG. 4C shows a distance between each navigation marker 440 indicated as L1'. The tolerance of this distance L1', and therefore the overall accuracy of the navigation array, may be the same as the tolerance of L1, as controlled by the single molding operation. The material used to mold the navigation array 430 may be translucent or transparent to one or more wavelengths of light in order for light rays (e.g., those emitted by a light source of a tracking system and/or subsequently observed by a sensor of the tracking system) to pass through the navigation marker lens 439 and reflect off the reflective material 441. In other embodiments, the material used to mold the navigation array 430 may be opaque and a reflective material may be applied to one or both sides of the navigation marker 440 to enable a navigation system tracking unit to detect the marker.

Figure 5:
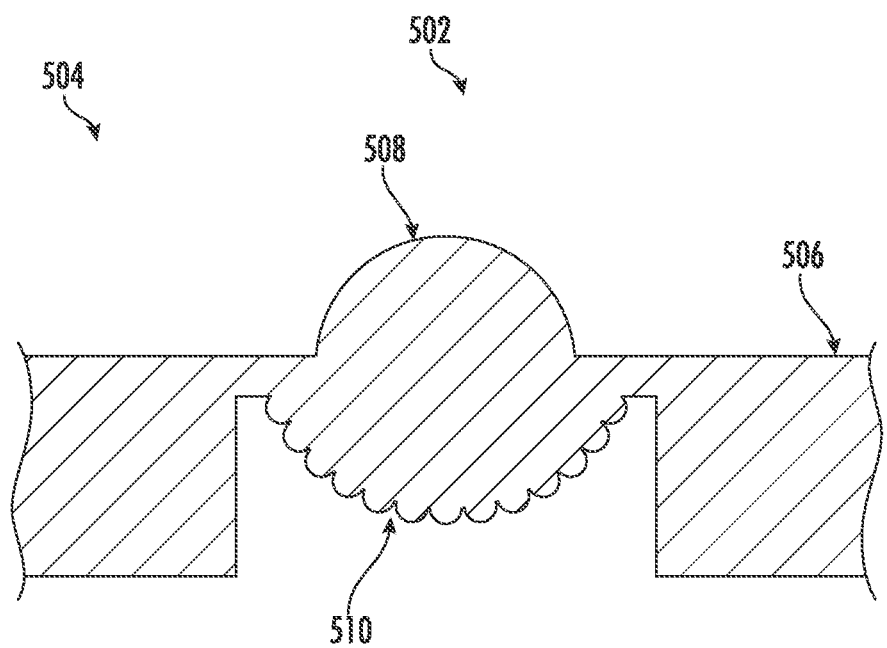
FIG. 5 shows a sectional view of a navigation marker region formed in a monolithic navigation array.

FIG. 5 illustrates a sectional view of a navigation marker region 502 formed in a monolithic (e.g., molded) navigation array 504 (e.g., such as described herein). In this embodiment, the navigation marker region 502 and a surrounding frame 506 are formed from a same material, e.g., a single piece, single material, array 504. A variety of navigation marker shapes may be employed, including the illustrated dual hemispherical surfaces that include an upper hemispherical surface 508 of a first diameter and a lower hemispherical surface 510 of a second diameter. In some embodiments, the lower hemispherical surface 510 may include various features formed thereon, such as a roughened surface that interacts with light differently from a smooth surface, etc. One or more of the upper hemispherical surface 508 and the lower hemispherical surface 510 may include a reflective material disposed thereon to aid a tracking unit in detecting the navigation marker.

The high accuracy navigation arrays disclosed herein may utilize any of a variety of navigation marker shapes and sizes. For example, upper and lower hemispherical surfaces may be of equal diameters or nonequal diameters. Although the above-described embodiments are spherical, in some embodiments, the presently described monolithic navigation arrays may utilize non-spherical navigation markers or a combination of spherical and non-spherical navigation markers.

Figure 6:
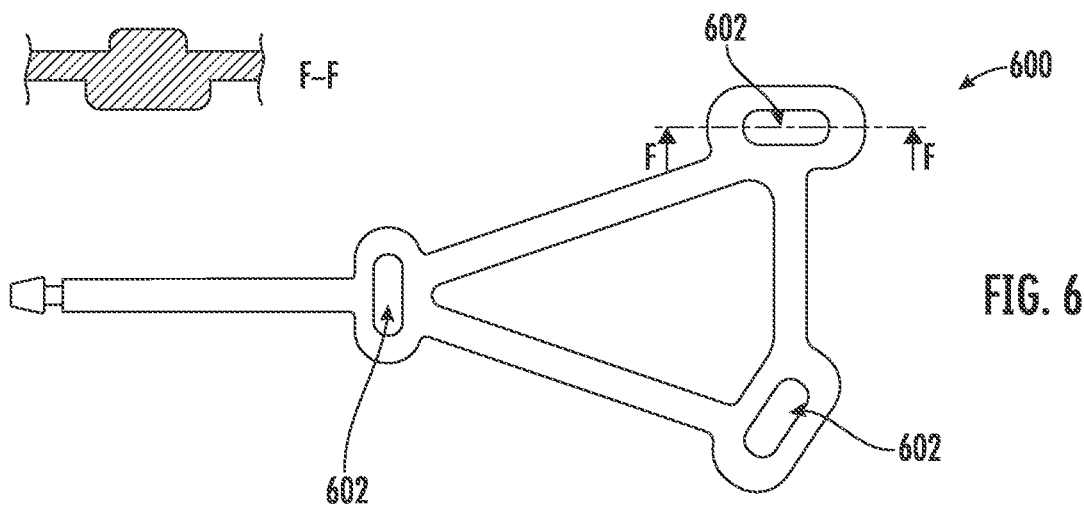
FIG. 6 shows another embodiment of a monolithic navigation array and a detail sectional view taken along a line F-F.

FIG. 6 shows a monolithic navigation array 600 having a plurality of non-spherical navigation markers 602. As can be seen in the detail sectional view taken along a line F-F, the navigation marker 602 has unequal diameters between its upper and lower sections.

Figure 7:
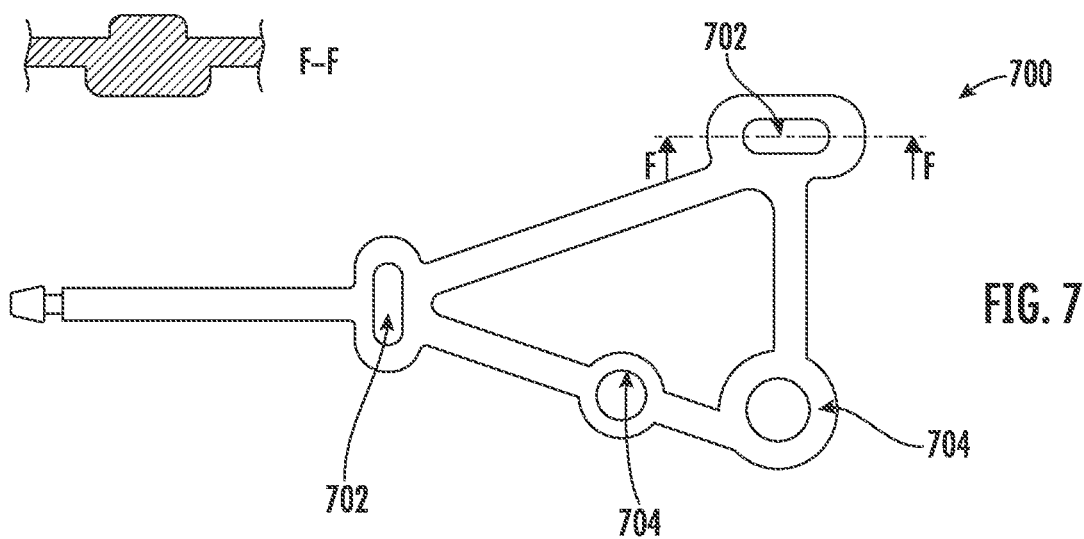
FIG. 7 shows another embodiment of a monolithic navigation array and a detail sectional view taken along a line F-F.

FIG. 7 shows a monolithic navigation array 700 having a plurality of non-spherical navigation markers 702 and a plurality of spherical navigation markers 704. As can be seen in the detail sectional view taken along a line F-F, the navigation marker 702 has unequal diameters between its upper and lower sections. In some embodiments, different shapes and/or sizes of navigation markers may be utilized to aid a surgical navigation system in more quickly recognizing and distinguishing between different arrays in its field of view.

In some embodiments, high accuracy navigation arrays may be molded from multiple materials into a single, monolithic navigation array wherein different regions are formed from different materials.

Figure 8A:
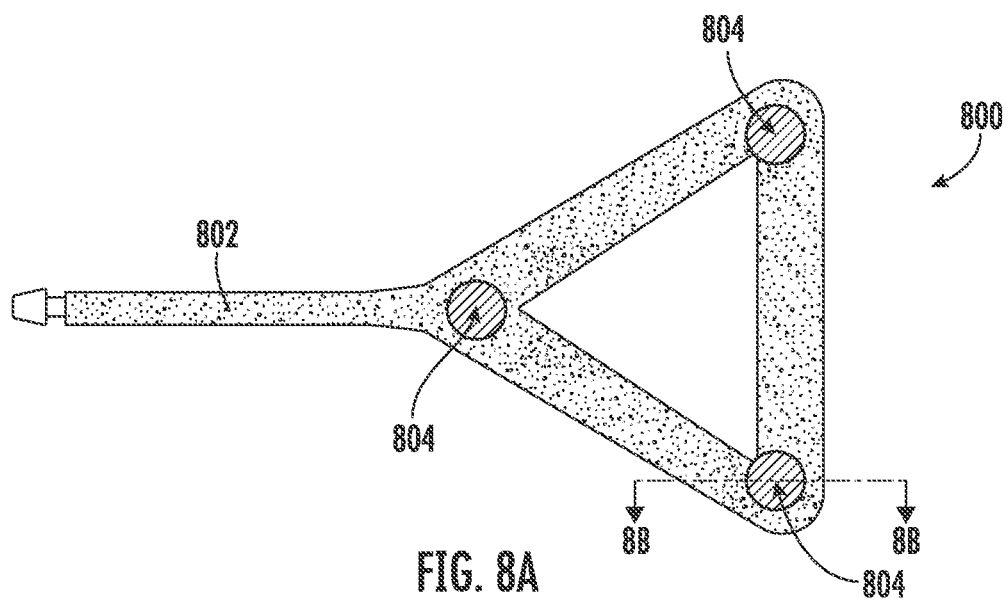
FIG. 8A shows another embodiment of a monolithic navigation array.
Figure 8B:
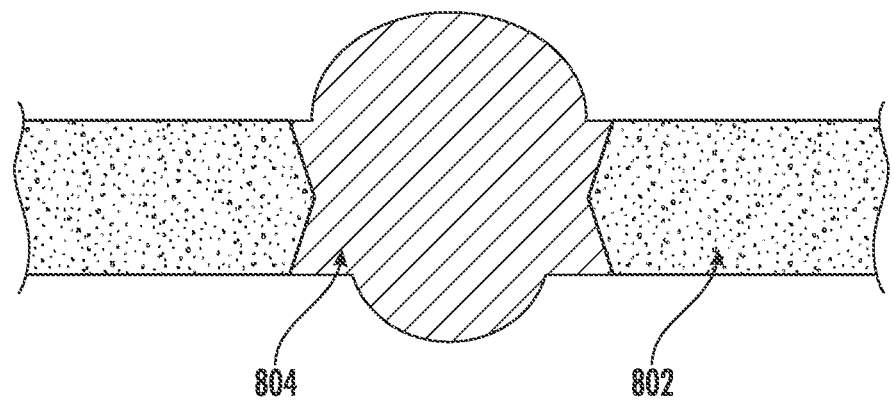
FIG. 8B shows a sectional view of a navigation marker region of the navigation array of FIG. 8A along the line 8B-8B.

FIGS. 8A and 8B show another embodiment of a monolithic navigation array 800. The array 800 is molded using two different materials, e.g., a matte-finish opaque material for the frame 802 and a transparent material for each of the navigation markers 804. An example method for producing the navigation array 800 may include a two-part molding operation that includes, for example, first molding the frame 802 using a plastic injection process and a matte opaque plastic, such as Polyether Ether Ketone (PEEK), Polysulfone (PSU), etc. Once the first material has sufficiently cooled following injection molding, the navigation markers 804 may be molded using a different transparent material, such as polycarbonate. In some embodiments, it may be desirable that the molding temperature of the material used to form the frame 802 is higher than the molding temperature of the material used to form the navigation markers 804, such that the second injection molding process does not melt the initially molded frame. Further, the shape utilized for the second molding operation may an undercut or other special shape to allow space for the material. In another embodiment, an acrylic material, such as Polymethyl Methacrylate (PMMA) or N,N-methylene-bis-acrylamide (MBA), may be utilized to perform over molding using a same material. In such an embodiment, for example, spherical navigation marker shapes may be in a core closure to have hermeticity, and chemical links may be formed with melting flows during the second injection.

FIG. 8B, in particular, illustrates a detail sectional view showing the different materials utilized in forming the navigation marker 804 and the navigation array frame 802. This embodiment also illustrates a navigation marker lens design unequal diameters between its upper and lower sections. At least one of these sections may be coated with a reflective material to enable a tracking unit to detect the navigation marker.

The molding processes disclosed herein may allow the formation of high accuracy navigation arrays at any desired size because both the frame and navigation markers are molded together. These may include arrays that utilize larger and smaller navigation makers than are commercially available to users.

Figure 9:
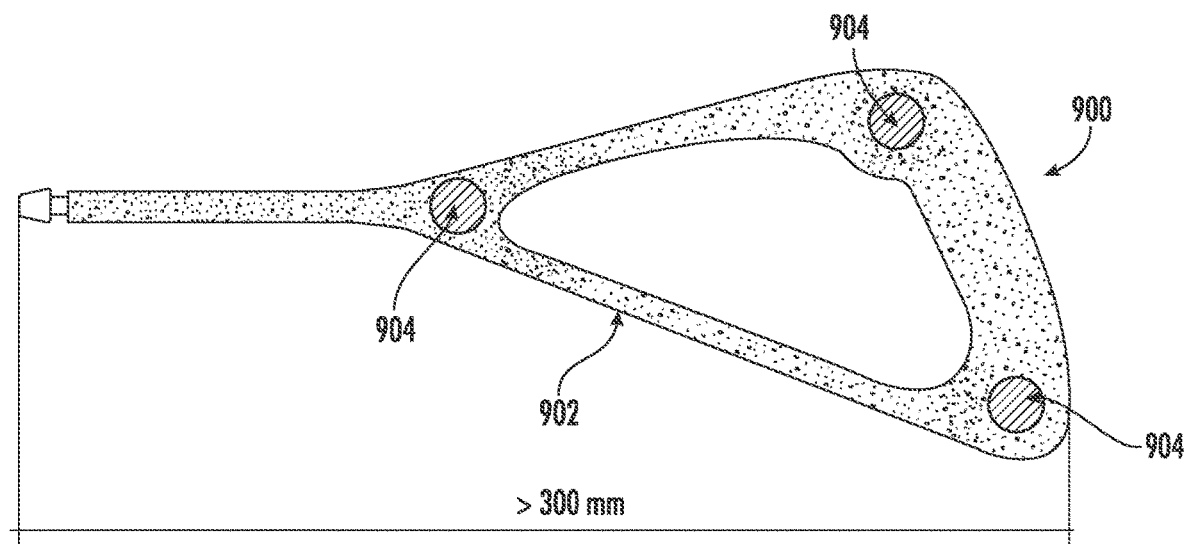
FIG. 9 shows another embodiment of a monolithic navigation array.
Figure 10:
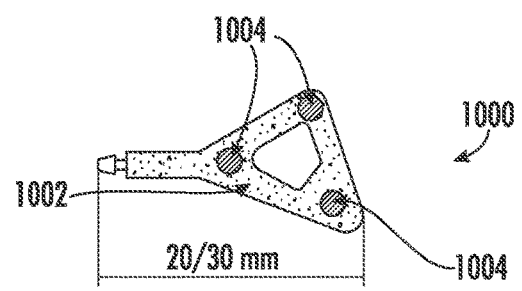
FIG. 10 shows another embodiment of a monolithic navigation array.

FIGS. 9 and 10 illustrate an example of a larger and smaller array, respectively. The navigation array 900 in FIG. 9 may have a frame 902 that spans 300 mm or more in overall length and may include navigation markers 904 that are about 13 mm in diameter, for example. In contrast, the navigation array 1000 in FIG. 10 may have a frame 1002 that spans between about 20 and about 30 mm in overall length and may include navigation markers 1004 that are about 5 mm in diameter, for example. Of course, any of a variety of sizes are possible, including, for example, arrays between about 50 mm and about 500 mm in overall length. As noted above, such arrays may include different numbers of navigation markers (of the same or different shapes) arranged in different geometric configurations. The ability to create custom and varying sizes of navigation arrays that include appropriately scaled navigation marker sizes may be helpful in tracking different types of instruments, portions of patient anatomy, or other components in a surgical field. For example, attaching a relatively large navigation array to a relatively smaller, more delicate surgical instrument may make operation of the instrument unwieldy for a user. In some instances, use of smaller navigation markers may introduce difficulties for the tracking unit to detect the markers and monitor the navigation array, but in many cases such issues may be resolved by repositioning the tracking unit to be closer to the arrays in use.

Another feature of the molded high accuracy navigation arrays disclosed herein is that they may be formed with navigation markers that may be visible on either side (e.g., both sides) of the navigation array. This may allow a single array to function in both "left" and "right" roles by simply rotating the array 180 degrees. Providing a single navigation array that may serve in either "left" or "right" roles during an operation would simplify require instrumentation and manufacturing.

Figure 11A:
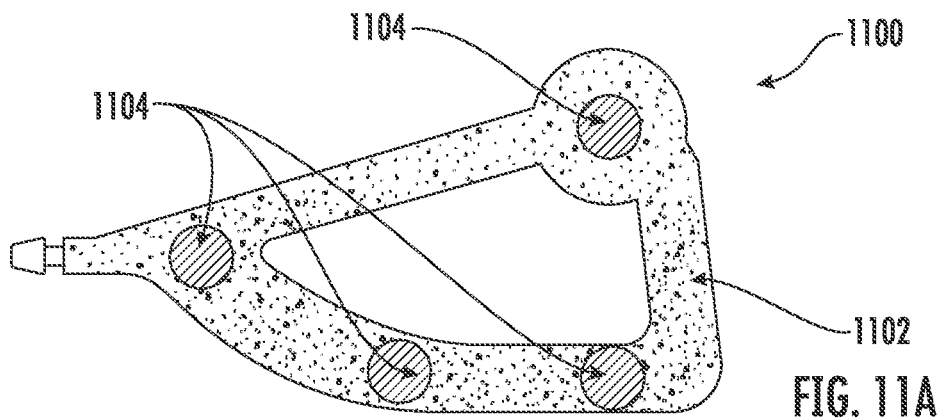
FIG. 11A shows another embodiment of a monolithic navigation array.
Figure 11B:
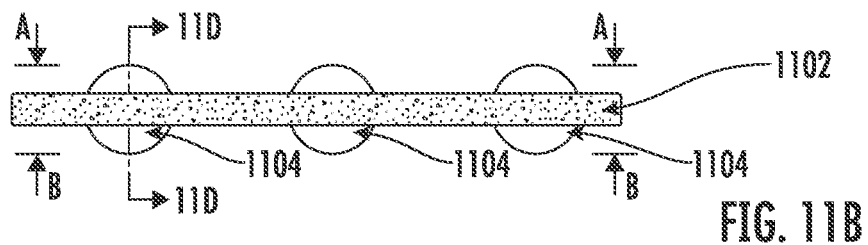
FIG. 11B shows an elevational view of the monolithic navigation array of FIG. 11A.
Figure 11C:
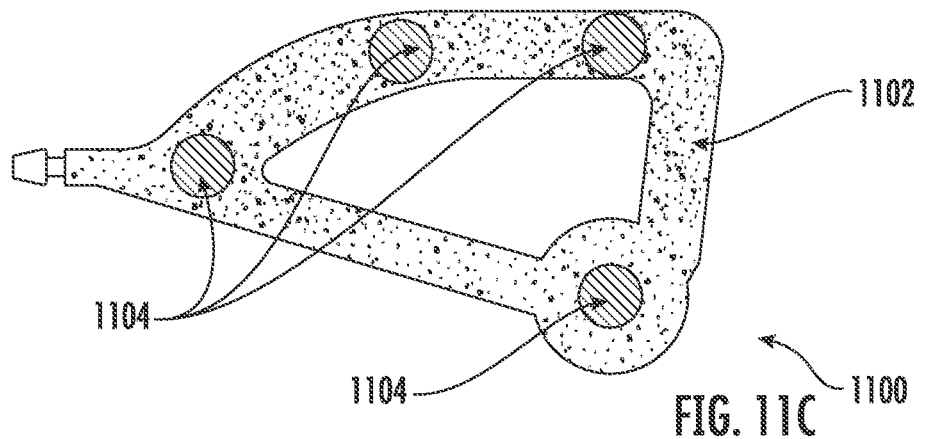
FIG. 11C shows a plan view of the monolithic navigation array of FIG. 11A.

FIGS. 11A-11D show another embodiment of a monolithic navigation array 1110, with a frame 1102 having a plurality of navigation markers 1104 that protrude from on opposite sides thereof, e.g., from both first and second sides of the frame. Turning to FIG. 11B, hemispherical surfaces of the navigation markers 1104 may be seen protruding from the surface of the frame 1104 on each side thereof. Comparing FIG. 11A and FIG. 11C, it is apparent that the array 1100 is adapted to function in both "left" and "right" roles by simply rotating the array 180 degrees, e.g., assuming each side of the navigation markers 1104 is coated with a reflective material or, alternatively, that a reflective material is embedded in each navigation marker 1104 and visible to a tracking unit from either side.

Figure 11D:
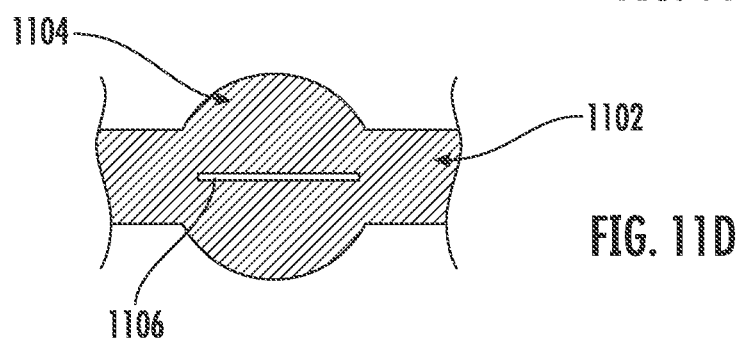
FIG. 11D shows a sectional view of a navigation marker region of the navigation array of FIG. 11B along the line 11D-11D.

FIG. 11D illustrates a sectional view and a reflective element 1106 that may be molded into a central region of the navigation marker 1104 to enable the navigation tracker 1104 to function from both sides of the navigation array 1100. For example, a piece of reflective material, such as a thin sheet of metal, may be disposed in the mold and over molded via the injection molding process that creates the monolithic navigation array 1100.

In certain embodiments, the molded high accuracy navigation arrays disclosed herein may be molded over an insert formed from a different material, such as a metal, ceramic, composite, or polymer. In this manner molding of the navigation array may be combined with an over molding process on the insert to again create a monolithic single part that includes the insert and over molded polymer to form a navigation array that does not include any mechanical interface for easily disassembling components. The insert may take a variety of forms, as described in more detail below.

Figure 12:
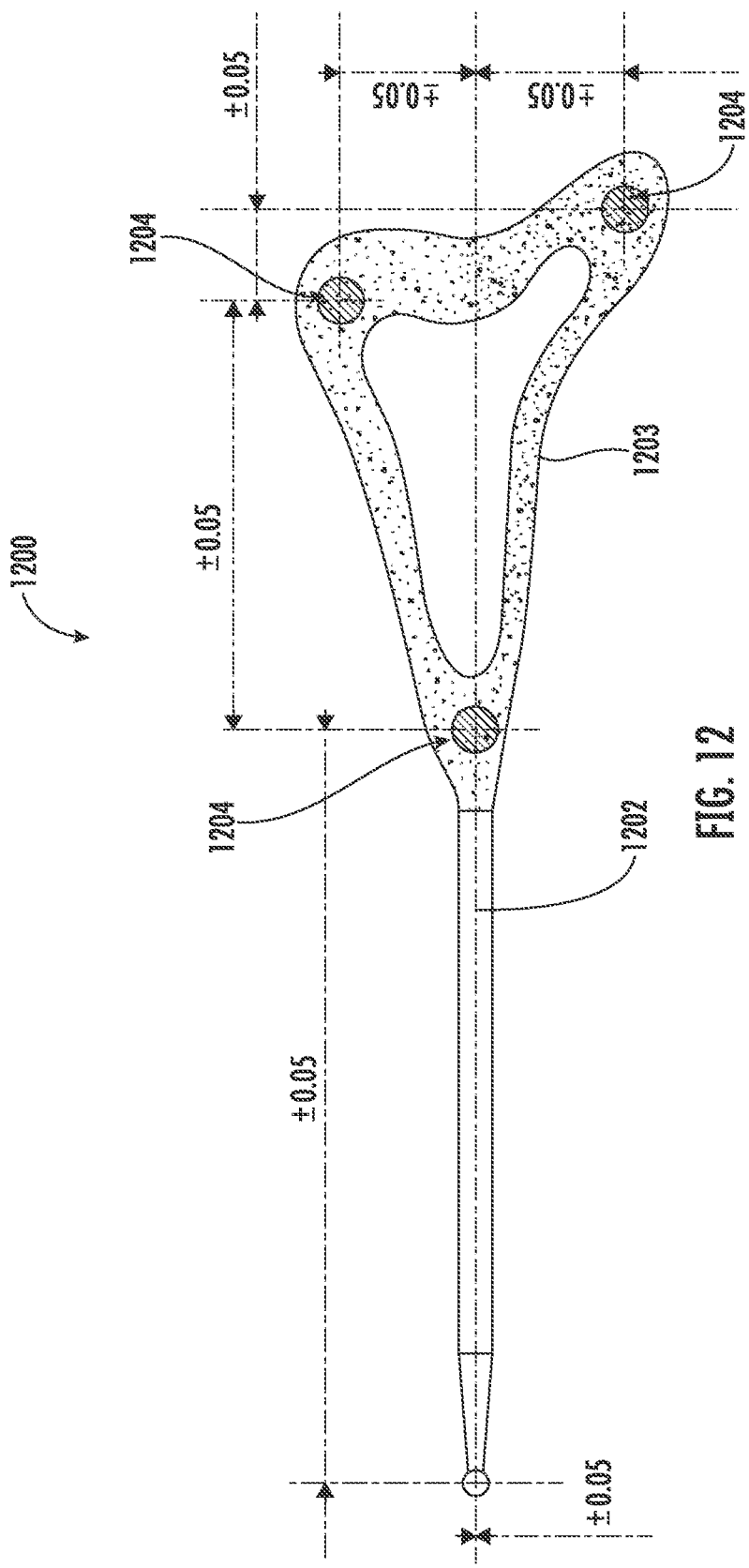
FIG. 12 shows another embodiment of a monolithic navigation array having, inter alia, an over molded insert.

FIG. 12 shows another embodiment of a monolithic navigation array 1200 having an over molded insert 1202, a frame 1203, and a plurality of navigation markers 1204. As can be appreciated, the molding process allows for tight tolerances between locations of the navigation markers 1204 and a distal end of the insert 1202, for example, within +/−0.05 mm. In some embodiments, the insert 1202 may be a metal, a ceramic, a plastic, or a composite, etc., integrally molded into the polymer injection molded frame 1203. The insert 1202 may include features to provide more secure coupling of the navigation array 1200 to a surgical instrument, robot arm, or other component. Alternatively, in some embodiments, the insert 1202 may itself form a surgical instrument, such as a landmark probe that may be used in conjunction with a surgical navigation system to register the location of various objects in the operating theater, such as various portions of patient anatomy, etc.

Various embodiments of distal-tip inserts that may be integrated into a monolithic navigation array via an over molding process are contemplated.

Figure 13:
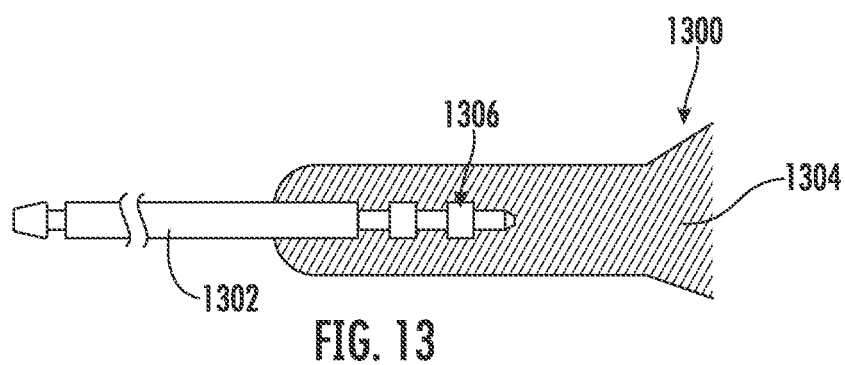
FIG. 13 shows a cut away view of another embodiment of an over molded insert.

FIG. 13 shows a cut away view of another embodiment of a monolithic navigation array 1300 having an over molded insert 1302. The insert 1302 is configured to couple with a surgical instrument or other component and is molded into the navigation array 1300 such that a proximal end 1306 thereof is over molded by a polymer frame 1304. The proximal end 1306 of the insert 1302 may include any of a variety of integrating features, such as portions of varying diameter with shoulder/ledge transitions to provide greater surface area for contact between the frame 1304 and the insert 1302. This junction between the insert 1302 and the frame 1304 may be designed to provide ample support to the insert. In some embodiments, for example, the frame 1304 may be over molded on top of the insert 1302 along a longitudinal axis thereof over a distance at least about 3 to 4 times a diameter of the insert.

Figure 14:
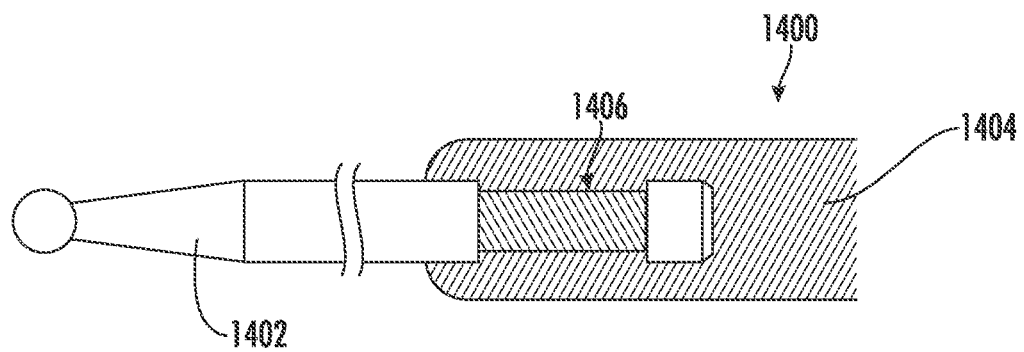
FIG. 14 shows a cut away view of another embodiment of an over molded insert.

FIG. 14 shows a cut away view of another embodiment of a monolithic navigation array 1400 having an over molded insert 1402. The insert 1402 is configured to operate as a landmarking probe and is molded into the navigation array 1400 such that a proximal end 1406 thereof is over molded by a polymer frame 1404. The proximal end portion 1406 of the insert 1402 may include a different configuration from the insert 1302 (FIG. 13), such as a knurled section of reduced diameter, again to increase surface area contact between the insert 1402 and frame 1404 and increase the support provided between these components. In some embodiments, for example, the frame 1404 may be over molded on top of the insert 1402 along a longitudinal axis thereof over a distance at least about 3 to 4 times a diameter of the insert.

Figure 15:
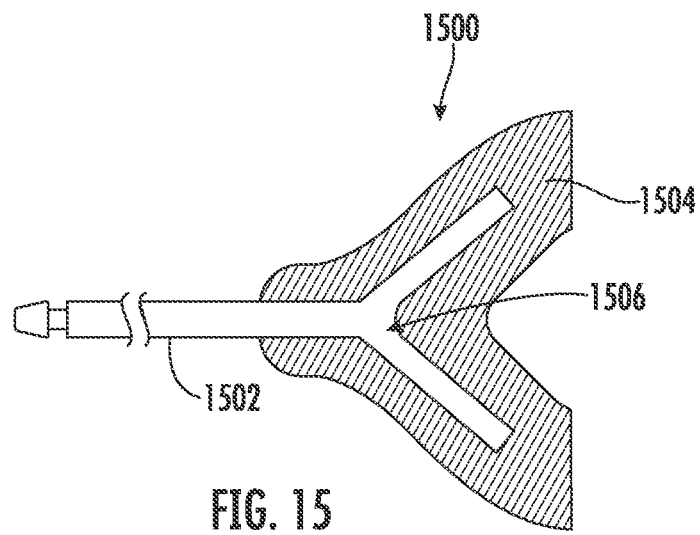
FIG. 15 shows a cut away view of another embodiment of an over molded insert.

FIG. 15 shows a cut away view of another embodiment of a monolithic navigation array 1500 having an over molded insert 1502. The insert 1502 is configured to couple to a surgical instrument or other component to be tracked and is molded into the navigation array 1500 such that a proximal end 1506 thereof is over molded by a polymer frame 1504. The proximal end portion 1506 of the insert 1502 may include a wishbone, forked, y-shaped, or multi-branch configuration to increase surface area contact between the insert 1502 and frame 1504 and increase the support provided between these components. In some embodiments, for example, the frame 1504 may be over molded on top of the insert 1502 along a longitudinal axis thereof over a distance at least about 3 to 4 times a diameter of the insert. In some embodiments, for example, the insert 1502 is configured to be used with relatively shorter arrays.

Figure 16A:
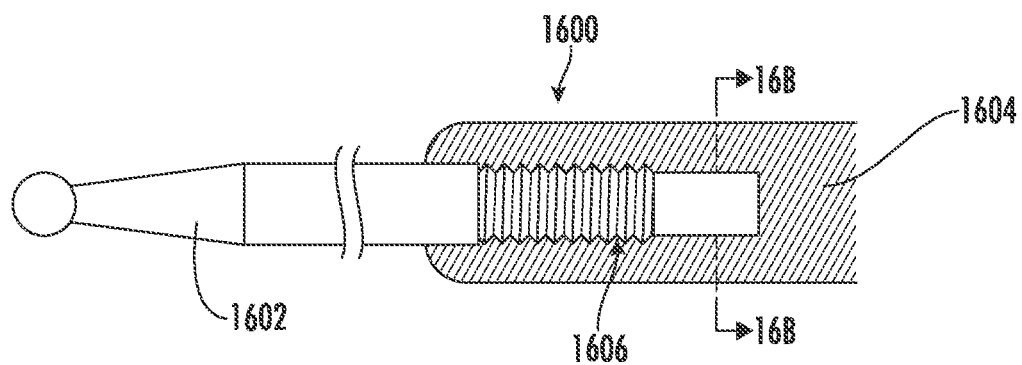
FIG. 16A shows a cut away view of another embodiment of an over molded insert.
Figure 16B:
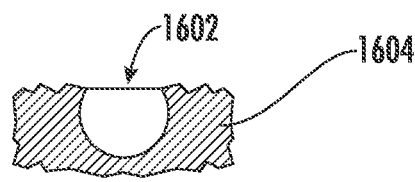
FIG. 16B shows a partial sectional view of the insert of FIG. 16A along the line 16B-16B.

FIG. 16A shows a cut away view of another embodiment of a monolithic navigation array 1600 having an over molded insert 1602. The insert 1602 is configured to operate as a landmarking probe and is molded into the navigation array 1600 such that a proximal end 1606 thereof is over molded by a polymer frame 1604. The proximal end portion 1606 of the insert 1602 may include a series of grooves to increase surface area contact between the insert 1602 and frame 1604 and increase the support provided between these components. Additionally, as best seen in FIG. 16B, the insert 1602 includes a flat portion to help prevent relative rotation between the insert 1602 and the frame 1604. In some embodiments, for example, the frame 1604 may be over molded on top of the insert 1602 along a longitudinal axis thereof over a distance at least about 3 to 4 times a diameter of the insert.

As may be appreciated, the inserts depicted in FIGS. 12-16B are not intended to be removable or disassembled from the remainder of the array.

In some embodiments, methods of manufacturing monolithic navigation arrays include providing a sub-assembly position reflective navigation markers and/or provide greater rigidity to the navigation array.

Figure 17:
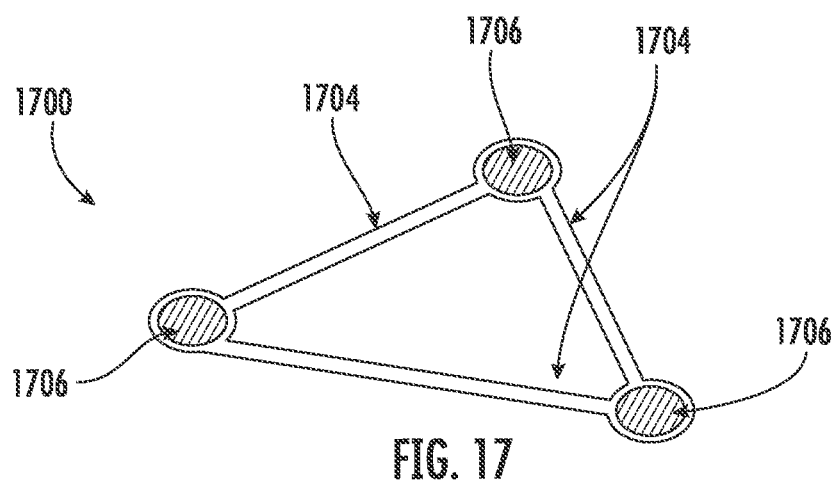
FIG. 17 shows a navigation marker sub-assembly.
Figure 18:
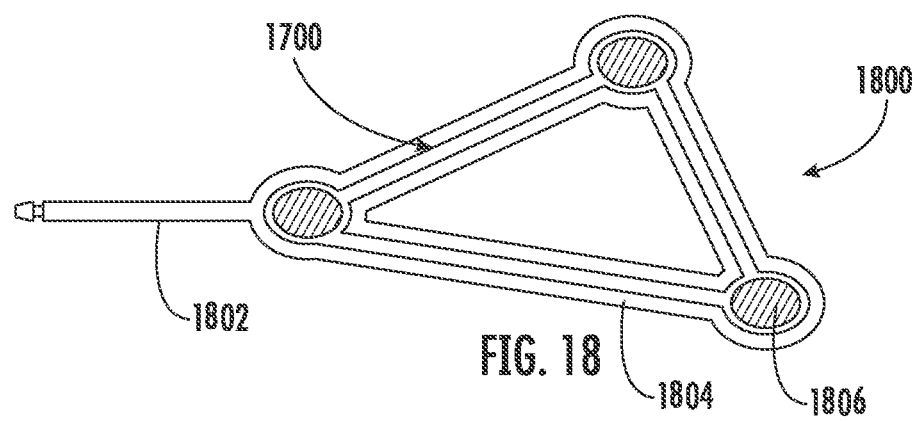
FIG. 18 shows a cut away view of another embodiment of a monolithic navigation array molded over the navigation marker sub-assembly of FIG. 17.

FIG. 17 shows a navigation marker sub-assembly 1700 that may be positioned within a mold and over molded with a polymer material to form a monolithic navigation array, such as monolithic navigation array 1800 shown in FIG. 18. The sub-assembly 1700 may include a plurality of segments 1704 that connect a plurality of navigation markers 1706 (e.g., or recesses configured to subsequently receive a transparent material during injection molding to form a navigation marker in the recess). Collectively, the segments 1704 and recesses could be referred to as a frame. In some embodiments, the segments 1704 may be formed from a metal. In some embodiments, the segments 1704 and recesses (to receive navigation markers 1706) may be molded as one component (e.g., a frame) during a first molding operation to create the sub-assembly 1700. The sub-assembly 1700 may then be positioned within a mold for the navigation array and over molded to create a monolithic navigation array 1800.

FIG. 18 shows a cut away view of the monolithic navigation array 1800 molded over the navigation marker sub-assembly 1700 of FIG. 17. The array 1800 comprises an end 1802 (which may be an insert), an injection molded frame 1804, and navigation markers 1806.

Figure 19:
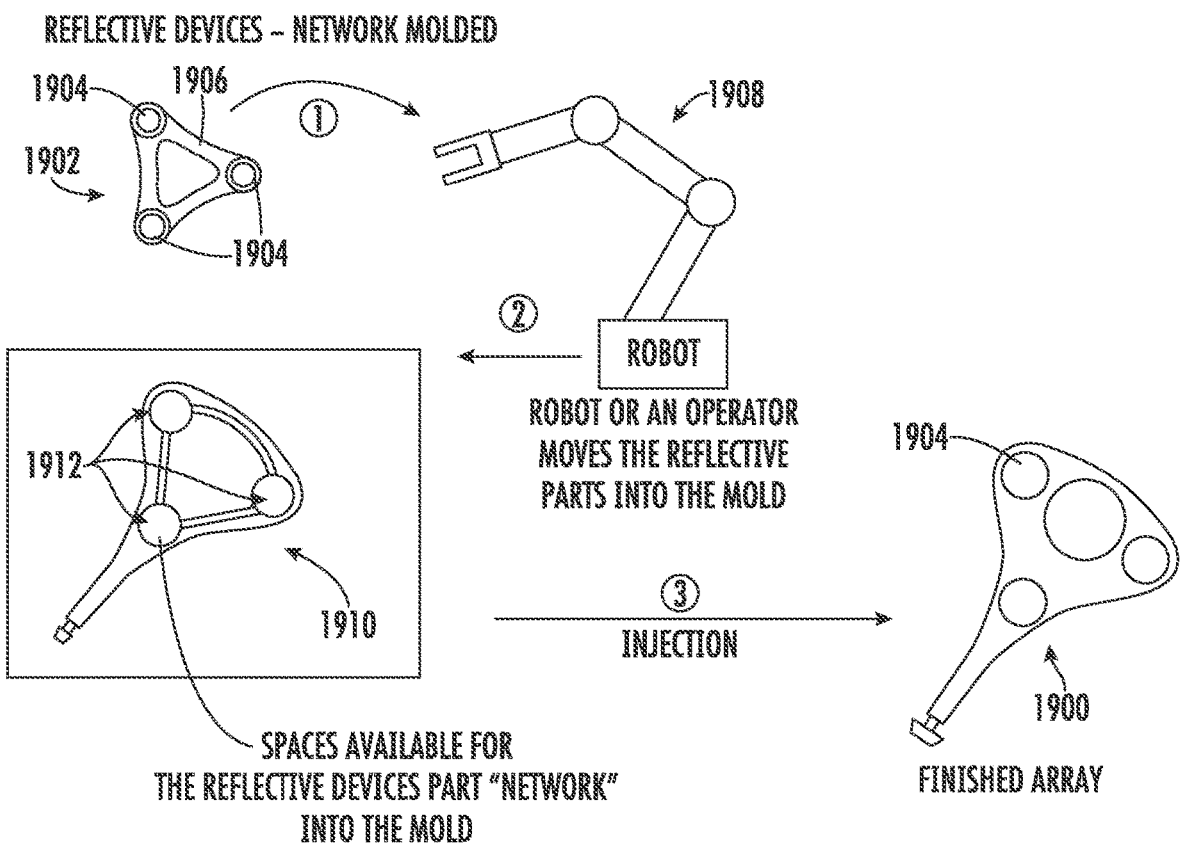
FIG. 19 shows a schematic of a method for molding a navigation array using a navigation marker sub-assembly.

FIG. 19 illustrates a method for creating a monolithic navigation array 1900 similar to the array 1800 (FIG. 18) that utilizes a sub-assembly 1902. The sub-assembly 1902 comprises a plurality of navigation markers 1904 (referred to as reflective devices in the figure) integrated into a frame 1906. At step 1, the sub-assembly 1902 is provided (e.g., the reflective navigation markers 1904 may be molded into the frame 1906).

At step 2, a manufacturing unit 1908 (e.g., a robot or an operator) loads the sub-assembly 1902 into a mold 1910 for the final navigation array 1900. The mold 1910 may include spaces 1912 formed in the mold to accommodate the sub-assembly 1902 (e.g., as a network of reflective devices) in a correct position. In addition, specific features formed in the mold 1910 may interact with features on the sub-assembly 1902 and/or navigation markers 1904 and/or frame 1906 (e.g., a ring around a part) to facilitate gripping the part by manufacturing unit 1908 and/or maintaining a position of the sub-assembly 1902 relative to the mold 1910 via features formed in the mold itself.

At step 3, an injection molding operation then over molds the sub-assembly 1902 to create the finished array 1900 having navigation markers 1904 correctly positioned thereon to provide accurate surgical navigation of any component coupled to the array. A variety of materials may be utilized for such a procedure. For example, in some embodiments the navigation markers 1904 may be formed from Polyethyleneimine (PEI), which has a high heat deflection temperature. For the over mold, a material with an adapted molding temperature may be utilized, such as Acrylonitrile Butadiene Styrene (ABS), N,N-methylene-bis-acrylamide (MBA), Polybutylene Terephthalate (PBT), etc.

Figure 20:
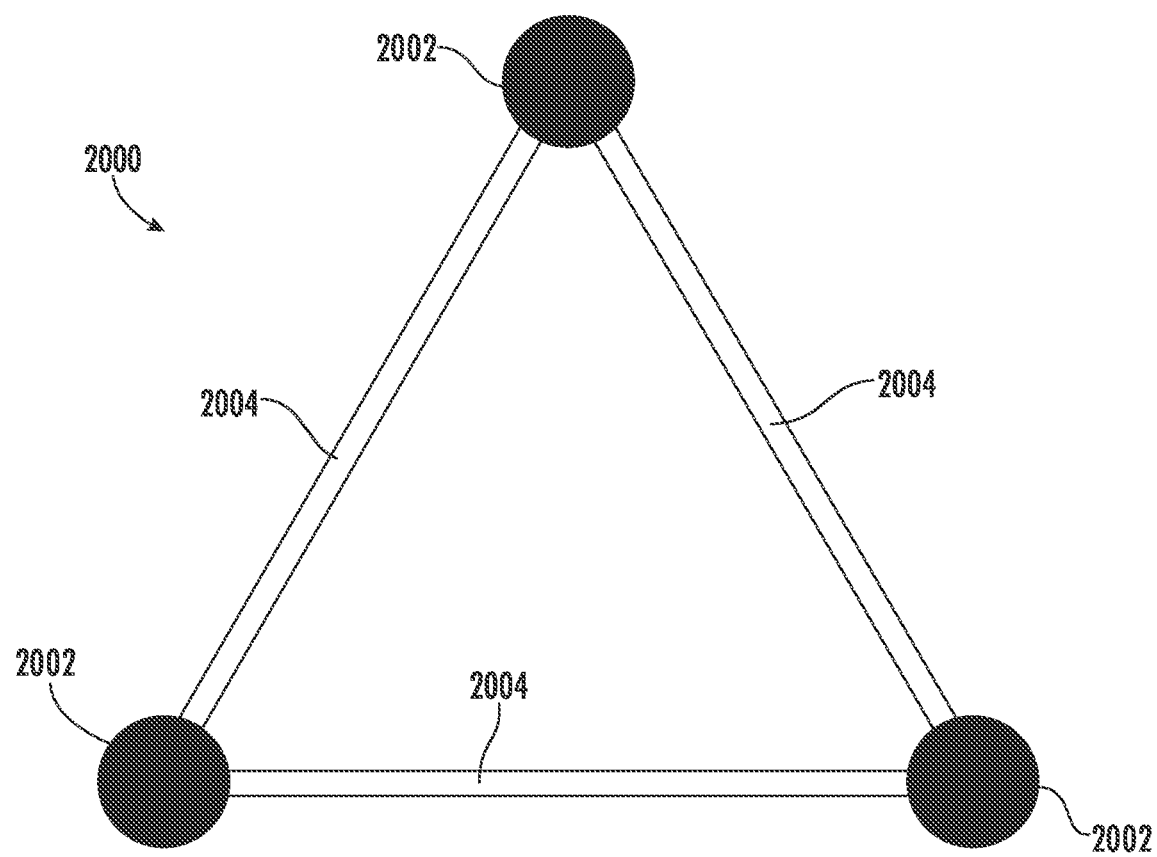
FIG. 20 shows another embodiment of a navigation marker sub-assembly.
Figure 21:
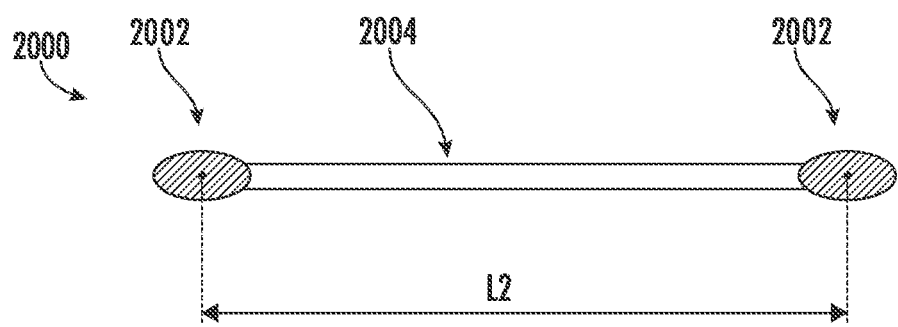
FIG. 21 shows an elevational view of the navigation marker sub-assembly of FIG. 20.

FIG. 20 shows a navigation marker sub-assembly 2000 comprising a plurality of reflective navigation markers 2002 (e.g., reflective elements that will serve as navigation markers in the finished array) connected by a plurality of arms 2004 in a shape to be subsequently over-molded to form a navigation array (such as monolithic navigation array 2200 of FIG. 22). FIG. 21 is an elevational view of the navigation marker sub-assembly 2000 and shows that the relative positions of each navigation marker 2002, as indicated by distance L2, are defined by the arms 2004. The tolerance of the navigation array frame positioning, however, does not necessarily define the resultant positional tolerance of the navigation markers.

Figure 22:
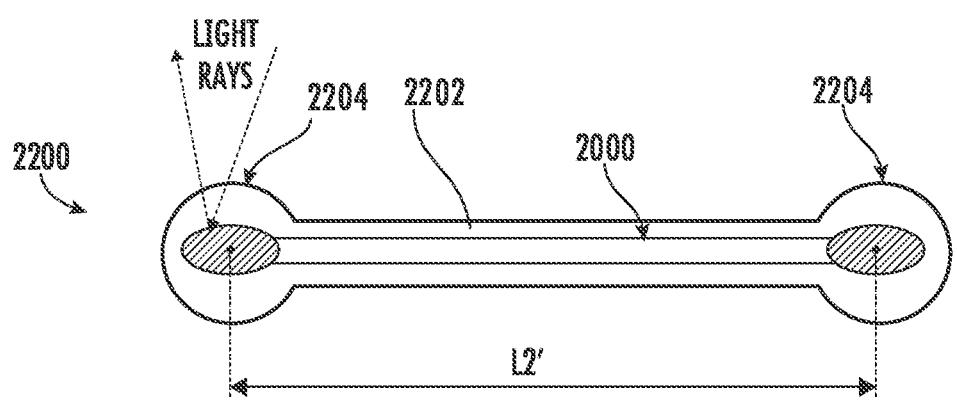
FIG. 22 shows a cut away view of another embodiment of a monolithic navigation array molded over the navigation marker sub-assembly of FIG. 20.

FIG. 22 shows a cut away view of another embodiment of a monolithic navigation array 2200 molded over the navigation marker sub-assembly 2000 (of FIG. 20). More particularly, in an over-molding step, such as a single molding operation, a material 2202 is molded around the frame 2000 to form a navigation array 2200. The navigation array 2200 includes navigation marker regions 2204 molded around the navigation markers 2002. The accuracy of the positioning of the navigation marker regions 2204 as indicated by L2', is controlled by the molding step and may be more tightly toleranced. The molding and over molding process described herein may create integrated, monolithic, single-piece navigation arrays that have greater tolerances than is typically encountered when manufacturing metal navigation array frames.

Figure 23:
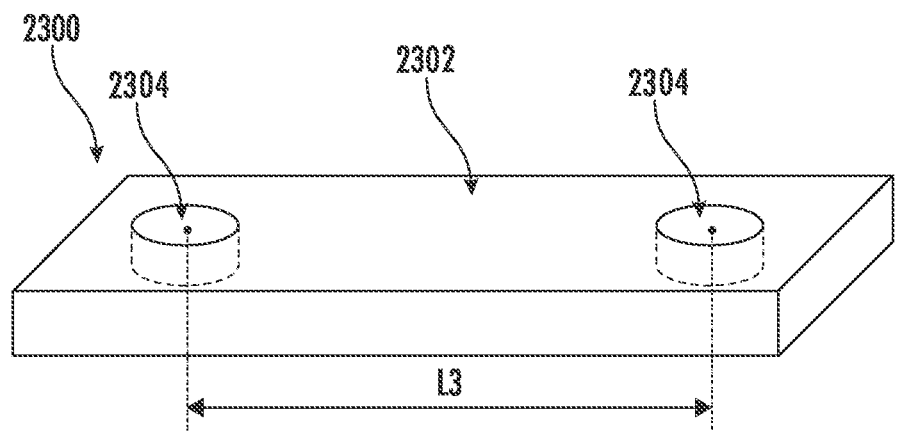
FIG. 23 shows another embodiment of a navigation marker sub-assembly.

FIG. 23 shows a navigation marker sub-assembly 2300 comprising a housing 2302 with voids 2304 defined therein, the voids configured to have navigation marker regions molded therein, the relative positions of the voids indicated by distance L3. In some instances, the navigation array sub-assembly 2300 may be molded in a first molding operation. Example materials for the housing 2302 may include opaque plastics, such as PSU and PEEK.

Figure 24:
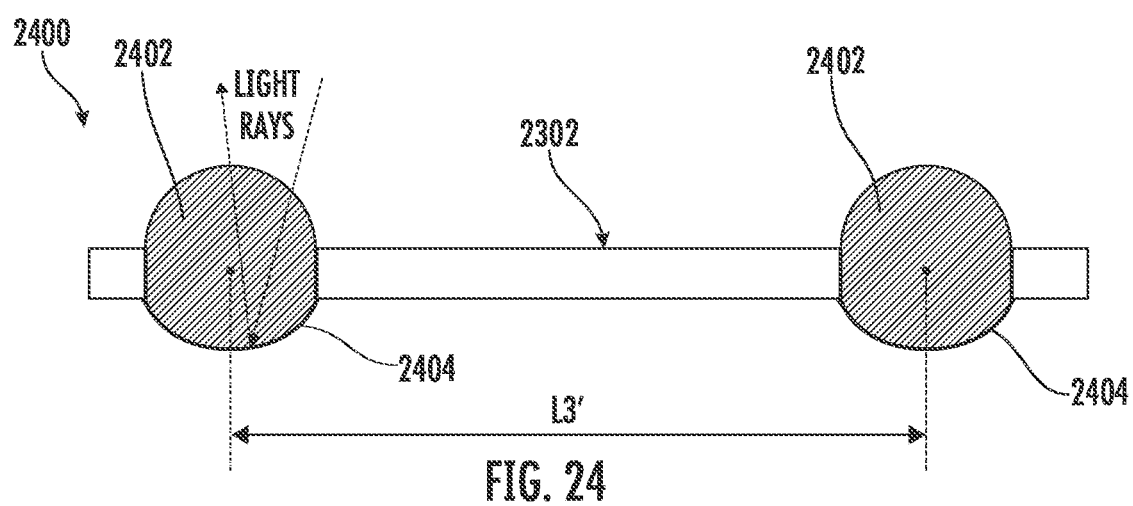
FIG. 24 shows navigation markers disposed in the navigation marker sub-assembly of FIG. 23.

In a second molding operation, as shown in FIG. 24, navigation markers 2402 are molded into the voids 2304 with a relative tolerance, as indicated by distance L3', that is controlled by the molding operating and may be more tightly toleranced. Example materials for the markers 2402 may be clear, such as polycarbonate. The housing 2302 material should have a higher molding temperature than the material for the markers 2402. Alternatively, the method may comprise over molding the markers 2402 with a same material as the housing 2302, such as with an acrylic material like PMMA or MBA, to have the housing form a chemical link with markers 2402 due to limited re-melting during the second injection molding step.

In a final step, reflective layers or coatings 2404 are applied to an exterior surface of the navigation markers 2402 to form navigation markers suitable for use with a surgical tracking unit of a surgical navigation system.

In still other embodiments, individual components may be over molded into a navigation array, similar to how the inserts described above were integrated into a navigation array via over molding. For example, and as shown in the method diagram of FIG. 25, in some embodiments, individual navigation markers or reflective devices 2502

Figure 25:
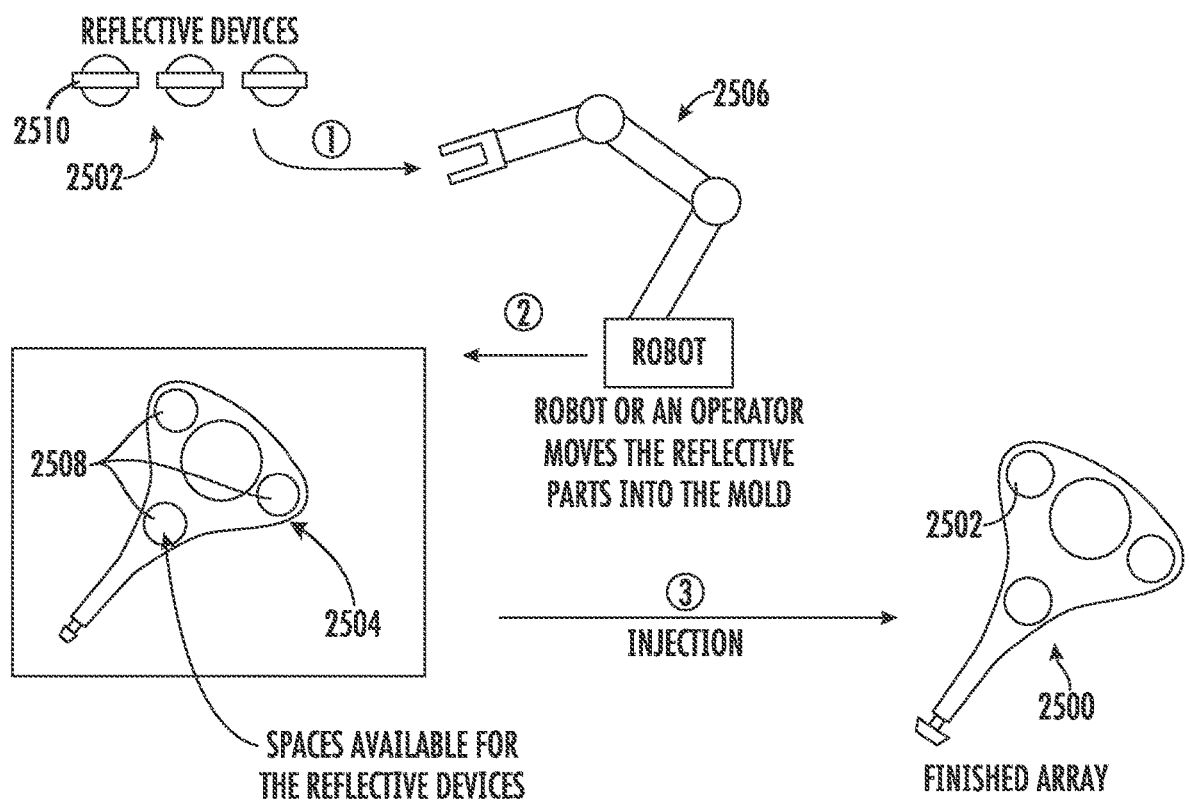
FIG. 25 shows a schematic of a method for molding a navigation array using individual navigation markers.

FIG. 25 illustrates a method for creating a monolithic navigation array 2500. At step 1, a plurality of individual navigation markers 2502 (referred to as reflective devices in the figure) are provided.

At step 2, a manufacturing unit 2506 (e.g., a robot or an operator) loads the individual navigation markers 2502 into a mold 2504 for the final navigation array 2500. The mold 2504 may include spaces 2508 formed in the mold to accommodate the navigation markers 2502. In addition, specific features formed in the mold may interact with features on the navigation markers 2502 (e.g., interface with a perimeter ring 2510 formed around a navigation marker 2502) to facilitate gripping the marker and maintaining its position relative to the mold 2504.

At step 3, an injection molding operation then over molds navigation markers 2502 to create the finished array 2500 having navigation markers 2502 correctly positioned thereon to provide accurate surgical navigation of any component coupled to the array. A variety of materials may be utilized for such a procedure. For example, in some embodiments the navigation markers 2502 may be formed from Polyethyleneimine (PEI), which has a high heat deflection temperature. For the over mold, a material with an adapted molding temperature may be utilized, such as Acrylonitrile Butadiene Styrene (ABS), N,N-methylene-bis-acrylamide (MBA), Polybutylene Terephthalate (PBT), etc.

Examples of the above-described embodiments may include the following.

In an example, a navigation array for use in a computer-assisted surgical system comprises a monolithic array body comprising a nonreflective frame region, and a plurality of spaced apart marker regions, wherein each of the marker regions has an associated reflective element configured to be detected and tracked by an optical tracking sensor. The frame region and the marker regions of the monolithic array body may be comprised of the same material. The material may be a polysulfone polymer or a polyether ether ketone polymer. The frame region of the monolithic array body may be comprised of a first material, and the marker regions of the monolithic array body may be comprised of a second material. The first material has a higher molding temperature than the second material in some examples. The first material may be an acrylonitrile butadiene styrene polymer, an N,N-methylene-bis-acrylamide polymer, a polybutylene terephthalate polymer, a polymethyl methacrylate polymer, or an N,N-methylene-bis-acrylamide polymer. The second material may be transparent. The second material may be a polycarbonate polymer or a polyethyleneimine polymer. The marker regions of the monolithic array body may be each coated with the reflective element. The reflective element may be embedded in each of the marker regions of the monolithic array body. The marker regions can be detected and tracked by the optical tracking sensor from either side of the navigation array. The marker regions of the monolithic array body may be all similarly shaped. At least two of the marker regions of the monolithic array body have different shapes. The marker regions of the monolithic array have unequal diameters between a first side of the array and a second side of the array. The navigation array may further comprise an insert over molded into the monolithic array body.

In another example, a computer assisted surgical system comprises the above-described navigation array embodiments, an optical tracking unit associated with at least one optical tracking sensor, and a control unit, wherein the control unit may be adapted to utilize a predetermined fixed geometric relationship between the marker regions and detected positions of the marker regions to determine a three-dimensional position and orientation of the navigation array. The computer assisted surgical system may further comprise a robot arm and a surgical instrument mounted to the robot arm. The navigation array may be adapted to be mounted to the robot arm or the surgical instrument.

In yet another example, a method manufacturing a navigation array comprises injection molding, in a single operation, the monolithic array body. The navigation array comprises the above-described navigation array embodiments.

In yet another example, a method manufacturing a navigation array comprises over molding the monolithic array body over a navigation marker sub-assembly. The navigation array comprises the above-described navigation array embodiments. The sub-assembly comprises a frame.

In yet another example, a method of producing a surgical navigation array comprises injection molding, in a single operation, a monolithic body of a surgical navigation array, the monolithic body comprising two or more marker regions located a distance apart from each other, and forming a navigation marker in each of the two or more marker regions by disposing a layer on at least a rear portion of an exterior of the marker region, wherein the layer and marker region together are configured to be detected and tracked using a optical surgical navigation system. A front portion of the exterior of the marker region in this example defines a hemispherical surface. The monolithic body in this example comprises a non-reflective outer surface. In this example, the layer comprises a reflective surface positioned against the rear portion. The reflective surface may be reflective to at least infrared light. The marker region may be made from a clear material that visibly exposes the reflective surface through a front portion of the exterior. A distance between the two or more marker regions as defined by the injection molding is accurate in this example to within 0.1 mm or less, 0.075 mm or less, or preferably, 0.05 mm, or less. The monolithic body may comprise three marker regions in a triangular arrangement. The monolithic body may be molded around a rigid frame. The monolithic body may be molded from polycarbonate.

In yet another example, a method of producing a surgical navigation array comprises injection molding, in a single operation, a monolithic body of a surgical navigation array on a frame comprising two or more reflective elements located apart from each other, the monolithic body defining a marker region around each of the two or more reflective elements such that the marker region and respective reflective element together form a navigation marker configured to be detected and tracked using a optical surgical navigation system, and wherein the two or more navigation markers are located a distance apart from each other that is defined by a position of their respective marker region in the monolithic body. The distance between the two or more marker regions as defined by the injection molding is accurate in this example to within 0.1 mm or less, 0.075 mm or less, or preferably, 0.05 mm, or less. The frame in this example comprises three reflective elements and the monolithic body comprises a marker region around each of the three reflective elements to form three navigation markers, and the three navigation markers are in a triangular arrangement. The frame in this example comprises three reflective elements, wherein the monolithic body comprises three marker regions, wherein each of the three reflective elements and a respective one of the three marker regions together from a navigation marker, and wherein the three navigation markers regions define a triangular arrangement. A front portion of an exterior of each marker region in this example defines a hemispherical surface above a respective reflective element. The monolithic body may comprise a non-reflective outer surface. The reflective element may be reflective to at least infrared light. Each marker region may be made from a clear material that visibly exposes the respective reflective element through an exposed exterior surface of the marker region.

In yet another example, a method of producing a surgical navigation array comprises injection molding, in a single operation, a monolithic body of a surgical navigation array around two or more surgical navigation markers, the monolithic body securely capturing the two or more surgical navigation markers in a define arrangement and a distance apart from each other, wherein each surgical navigation marker is configured and positioned in the monolith body to be detected and tracked using a optical surgical navigation system. In this example, the monolithic body securely captures three navigation markets in a triangular arrangement. The distance between the two or more marker regions may be accurate in this example to within 0.1 mm or less, 0.075 mm or less, or preferably, 0.05 mm, or less.

In yet another example, a method of producing a surgical navigation array comprises injection molding, in a first operation, a monolithic frame of a surgical navigation array, the monolithic body defining two or more voids, injection molding, in a single second operation, a monolithic marker element in each of the two or more voids, and forming a navigation marker from each of the two or more marker elements by disposing a layer on at least portion of an exterior of the marker element, wherein the layer and marker element together are configured to be detected and tracked using a optical surgical navigation system. In this example, the monolithic body comprises a first material and the monolithic marker element comprises a second material that is different from the first material. The first material may define a nonreflective surface of the monolithic frame, and the second material may be clear such a reflective surface of the layer is visible through the marker element. A front portion of the exterior of the marker region may define a hemispherical surface. The monolithic body may comprise a non-reflective outer surface. The layer may comprise a reflective surface positioned against the rear portion. The reflective surface may be reflective to at least infrared light. The marker region may be made from a clear material that visibly exposes the reflective surface through a front portion of the exterior. The distance between marker elements may be accurate in this example to within 0.1 mm or less, 0.075 mm or less, or preferably, 0.05 mm, or less. The monolithic body may comprise three marker regions in a triangular arrangement.

In yet another example, a method of producing a surgical navigation array on a frame comprises injection molding, in a single second operation, a two or more marker elements on the frame, and forming a navigation marker from each of the two or more marker elements by disposing a layer on at least portion of an exterior of the marker element, wherein the layer and marker element together are configured to be detected and tracked using a optical surgical navigation system. The method may further comprise injection molding three marker elements on the frame in a triangular arrangement and forming a navigation marker from each of the three marker elements. The injection molding may locate each of the two or more market elements a respective distance from each other that is accurate to within 0.1 mm or less. A front portion of the exterior of the marker element may defines a hemispherical surface. The frame may comprise a non-reflective outer surface. The layer may comprise a reflective surface positioned against the rear portion. The reflective surface may be reflective to at least infrared light. The marker element may be made from a clear material that visibly exposes the reflective surface through a front portion of the exterior. The method may further comprise injection molding, in a single second operation, three marker elements on the frame and forming a navigation marker from each of the three marker elements.

In yet another example, a surgical navigation array comprises an injection-molded monolithic body defining a frame region and a plurality of navigation marker regions connected by the frame region, each of the navigation marker regions defining a clear front exterior surface and a rear exterior surface, a reflective layer disposed on the rear exterior surface of each of the navigation marker regions, wherein each of the navigation marker regions and a respective reflective layer formed on a navigation marker region is configured to be detected and tracked using a surgical navigation system. The clear front exterior may form a hemispherical shape. The frame region may comprise a nonreflective exterior surface. The frame region may be formed from a first material and each of the marker regions is formed from a second material that is different from the first material. A rigid frame may surround the injection-molded monolithic body. The plurality of navigation marker regions may include three navigation marker regions connected in a triangular configuration.

The invention claimed is:

1. A navigation array for use in a computer-assisted surgical system, the array comprising:
   a single-piece molded array body comprising:
      a nonreflective frame region; and
      a plurality of spaced apart marker regions;
   wherein each of the marker regions has an associated reflective element configured to be detected and tracked by an optical tracking sensor.

2. The navigation array of claim 1, wherein the frame region and the marker regions of the array body are comprised of the same material.

3. The navigation array of claim 2, wherein the material is a polysulfone polymer or a polyether ether ketone polymer.

4. The navigation array of claim 1, wherein the frame region of the array body is comprised of a first material, and the marker regions of the array body are comprised of a second material.

5. The navigation array of claim 4, wherein the first material has a higher molding temperature than the second material.

6. The navigation array of claim 4, wherein the first material is an acrylonitrile butadiene styrene polymer, an N,N-methylene-bis-acrylamide polymer, a polybutylene terephthalate polymer, a polymethyl methacrylate polymer, or an N,N-methylene-bis-acrylamide polymer.

7. The navigation array of claim 4, wherein the second material is transparent.

8. The navigation array of claim 4, wherein the second material is a polycarbonate polymer or a polyethyleneimine polymer.

9. The navigation array of claim 1, wherein the marker regions of the array body are each coated with the reflective element.

10. The navigation array of claim 1, wherein the reflective element is embedded in each of the marker regions of the array body.

11. The navigation array of claim 10, wherein the marker regions can be detected and tracked by the optical tracking sensor from either side of the navigation array.

12. The navigation array of claim 1, wherein the marker regions of the array body are all similarly shaped.

13. The navigation array of claim 1, wherein at least two of the marker regions of the array body have different shapes.

14. The navigation array of claim 1, wherein the marker regions of the array have unequal diameters between a first side of the array and a second side of the array.

15. The navigation array of claim 1, further comprising an insert over molded into the array body.

16. A computer assisted surgical system, the system comprising:
   a navigation array of claim 1;
   an optical tracking unit associated with at least one optical tracking sensor; and
   a control unit, wherein the control unit is adapted to utilize a predetermined fixed geometric relationship between the marker regions and detected positions of the marker regions to determine a three-dimensional position and orientation of the navigation array.

17. The system of claim 16, further comprising a robot arm and a surgical instrument mounted to the robot arm.

18. The system of claim 17, wherein the navigation array is adapted to be mounted to the robot arm or the surgical instrument.

19. A method manufacturing a navigation array of claim 1, comprising:
   injection molding, in a single operation, the array body.

20. A method manufacturing a navigation array of claim 1, comprising:
   over molding the array body over a navigation marker sub-assembly.

* * * * *